US011666622B2

(12) United States Patent
Naone

(10) Patent No.: US 11,666,622 B2
(45) Date of Patent: Jun. 6, 2023

(54) TOPICAL TREATMENT FOR ANIMALS

(71) Applicant: Crystal-Ray Kanoelani Naone, Thousand Oaks, CA (US)

(72) Inventor: Crystal-Ray Kanoelani Naone, Thousand Oaks, CA (US)

(73) Assignee: LA'AU INC., Thousand Oaks, CA (US)

( * ) Notice: Subject to any disclaimer, the term of this patent is extended or adjusted under 35 U.S.C. 154(b) by 0 days.

(21) Appl. No.: 17/092,150

(22) Filed: Nov. 6, 2020

(65) Prior Publication Data

US 2021/0128666 A1 May 6, 2021

Related U.S. Application Data

(60) Provisional application No. 62/931,543, filed on Nov. 6, 2019.

(51) Int. Cl.

| | |
|---|---|
| ***A61K 36/886*** | (2006.01) |
| ***A61K 33/04*** | (2006.01) |
| ***A61K 31/716*** | (2006.01) |
| ***A61K 47/06*** | (2006.01) |
| ***A61P 17/02*** | (2006.01) |
| ***A61K 9/16*** | (2006.01) |

(52) U.S. Cl.

CPC .......... *A61K 36/886* (2013.01); *A61K 9/1688* (2013.01); *A61K 31/716* (2013.01); *A61K 33/04* (2013.01); *A61K 47/06* (2013.01); *A61P 17/02* (2018.01); *A61K 2236/31* (2013.01)

(58) Field of Classification Search

None

See application file for complete search history.

(56) References Cited

U.S. PATENT DOCUMENTS

2011/0165276 A1* 7/2011 Coley .................... A61P 17/02 424/744

OTHER PUBLICATIONS https://strawfieldpets.com/blogs/news/how-to-treat-dog-wounds-at-home (Year: 2017).*

Foley et al., "A synthetic review of notoedres species mites and mange", journal first published online Sep. 9, 2016, https://www.cambridge.org/core/journals/parasitology/article/synthetic-review-of-notoedres-species-mites-and-mange/E2858200FA246AD3264C0F9648E60F37, last accessed Nov. 6, 2020, 15 total pages.

Neil Howie, "Mange and udder cleft dermatitis in cattle", journal Jul. 5, 2017, 3 total pages.

Salehi et al., "Aloe Genus Plants: From Farm to Food Applications and Phytopharmacotherapy" Int. J. Mol. Sci. 2018, 19, 2843, Sep. 19, 2018, 49 total pages.

Kesarwani et al., "Bioavailability enhancers of herbal origin: An overview", Department of Pharmacognosy, Faculty of Pharmacy, Babu Banarasi Das National Institute of Technology and Management (BBD University), BBD Green City, Lucknow, U.P., 227105, India, published Apr. 2013, 14 total pages.

Norman et al, "Antiseptics for burns (Review)", Cochrane Database of Systematic Reviews 2017, Issue 7. Art. No. CD011821, published Jul. 2017,total of 240 pages.

Passafiume et al., "Effect of Three Different Aloe vera Gel-Based Edible Coatings on the Quality of Fresh-Cut "Hayward" Kiwifruits", Department of Agricultural, Food and Forest Sciences (SAAF), Published Jul. 16, 2020. 17 total pages.

Eid et al., "Public Knowledge, Attitude, and Practice on Herbal Remedies Used During Pregnancy and Lactation in West Bank Palestine", Department of Pharmacy, Faculty of Medicine and Health Sciences, Published Feb. 14, 2020, https://www.frontiersin.org/articles/10.3389/fphar.2020.00046/full. 10 total pages.

Begum Yurdakok-Dikme et al., "Herbal Bioenhancers in Veterinary Phytomedicine", Department of Pharmacology and Toxicology, Faculty of Veterinary Medicine, Ankara University, Ankara, Turkey, Published Oct. 10, 2018, https://www.frontiersin.org/articles/10.3389/fvets.2018.00249/full, 8 total pages.

Etemad et al., Delayed Complications and LongTerm Management of Sulfur Mustard Poisoning: A Narrative Review of Recent Advances by Iranian Researchers Part II: Clinical Management and Therapy, Article, Iran J Med Sci May 2018; vol. 43 No. 3 23, published May 2018, 13 pages.

Mila-Kierzenkowska et al., "Comparative Efficacy of Topical Pertmehrin, Crotamiton and Sulfur Ointment in Treatment of Scabies", J Arthropod-Borne Dis, Mar. 2017, 11(1): pp. 1-9.

Shetty et al., "Anticandidal efficacy of denture cleansing tablet, Triphala, Aloe vera, and Cashew leaf on complete dentures of institutionalized elderly", Article, Journal of Ayurveda & Integrative Medicine | Jan.-Mar. 2014 | vol. 5 Issue 1, 4 pages.

Thomas W. Sawyer, "N-Acetylcysteine as a treatment for sulphur mustard poisoning", Defence Research & Development Canada, Suffield Research Centre, published Sep. 25, 2020, 16 total pages.

KumAr et al., Comparison of Plaque Inhibiting Efficacies of Aloe Vera and Propolis Tooth Gels: A Randomized PCR Study, Journal of Clinical and Diagnostic Research. Sep. 2015, vol. 9(9): ZC01-ZC03, 3 pages.

Moghaddam et al., "Clinical Evaluation of Effects of Local Application of Aloe vera Gel as an Adjunct to Scaling and Root Planning in Patients with Chronic Periodontitis", J Dent Shiraz Univ Med Sci., Sep. 2017; 18(3): 165-172, 8 total pages.

Chavan et al., "Pharmaceutical Standardization and Physicochemical Characterization of Traditional Ayurvedic Marine Drug: Incinerated Conch Shell (*Shankha bhasma*)", Article, Mar. Drugs 2018, 16, 450; doi:10.3390/md16110450, published Nov. 15, 2018, 20 pages.

(Continued)

*Primary Examiner* — Jessica Worsham

(74) *Attorney, Agent, or Firm* — SoCal IP Law Group LLP; Brian S. Tamsut; Jonathan Pearce

(57) ABSTRACT

A topical formulation and method of using the formulation on animals including dogs is disclosed. The formulation is used to facilitate the healing of cuts, scrapes, abrasions, and other conditions often experienced by animals. A main ingredient of the formulation is sulfur in a high concentration.

1 Claim, 6 Drawing Sheets

Specification includes a Sequence Listing.

(56) References Cited

OTHER PUBLICATIONS

Josias H. Hamman, "Composition and Applications of Aloe vera Leaf Gel", Molecules 2008, 13, 1599-1616; DOI: 10.3390/molecules13081599, Published Aug. 8, 2008, 18 pages.
Fox et al., "Transdermal Drug Delivery Enhancement by Compounds of Natural Origin", Molecules 2011, 16, 10507-10540; doi:10.3390/molecules161210507, published Dec. 16, 2011, 34 pages.
Unuofin et al., "Antioxidant Effects and Mechanisms of Medicinal Plants and Their Bioactive Compounds for the Prevention and Treatment of Type 2 Diabetes: An Updated Review", Article, Hindawi Oxidative Medicine and Cellular Longevity vol. 2020, Article ID 1356893, 36 pages https://doi.org/10.1155/2020/1356893, published Feb. 14, 2020, 36 pages.
Moore et al., "An online survey of personal mosquitorepellent strategies", journal, https://peerj.com/articles/5151/, published Jul. 3, 2018, 25 pages.
Vet Record, "Psoroptic mange in cattle in Scotland", Veterinary Record: first published as 10.1136/vr.k1360 on Mar. 23, 2018. Downloaded from http://veterinaryrecord.bmj.com/ on May 6, 2018, 4 pages.
William Abramovits, "Rosac Cream With Sunscreens (sodium sulfacetamide 10% and sulfur 5%", Baylor College of Medicine, published Mar. 2004, 1 page.
Kasper et al., "Effects of Dilution Systems in Olfactometry on the Recovery of Typical Livestock Odorants Determined by PTR-MS", article, Sensors 2017, 17, 1859; doi:10.3390/s17081859, published Aug. 11, 2017, 16 pages.
Dudhatra et al., A Comprehensive Review on Pharmacotherapeutics of Herbal Bioenhancers, article, The Scientific World Journal, vol. 2012, Article ID 637953, 33 pages, published Aug. 9, 2012.
Philips et al., "Comprehensive review of hepatotoxicity associated with traditional Indian Ayurvedic herbs", World J Hepatol published Sep. 27, 2020; 12(9): 574-595.

* cited by examiner

TOPICAL TREATMENT FOR ANIMALS

RELATED APPLICATIONS

This application claims priority to U.S. provisional application No. 62/931,543 filed on Nov. 6, 2019 and entitled "Topical Treatment for Animals."

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

SEQUENCE LISTING

The instant application contains a Sequence Listing which has been submitted in ASCII format via EFS-Web and is hereby incorporated by reference in its entirety. The ASCII copy, created on Nov. 2, 2020 is named TOPICAL TREATMENT FOR ANIMALS_ST25.txt and is 11,151 bytes in size.

BACKGROUND

Field

This disclosure relates to topical skin creams for use by animals such as domestic animals, farm animals, or wild animals.

DETAILED DESCRIPTION

Figure 1:
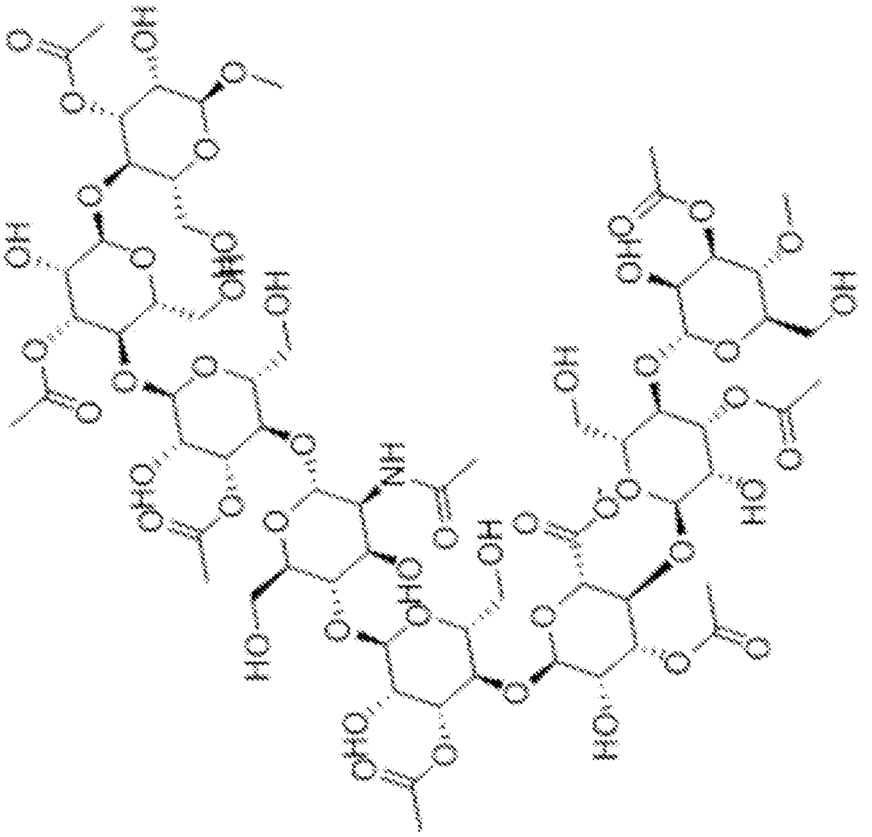
FIG. 1 is a molecular diagram of Acemannan
Figure 2:
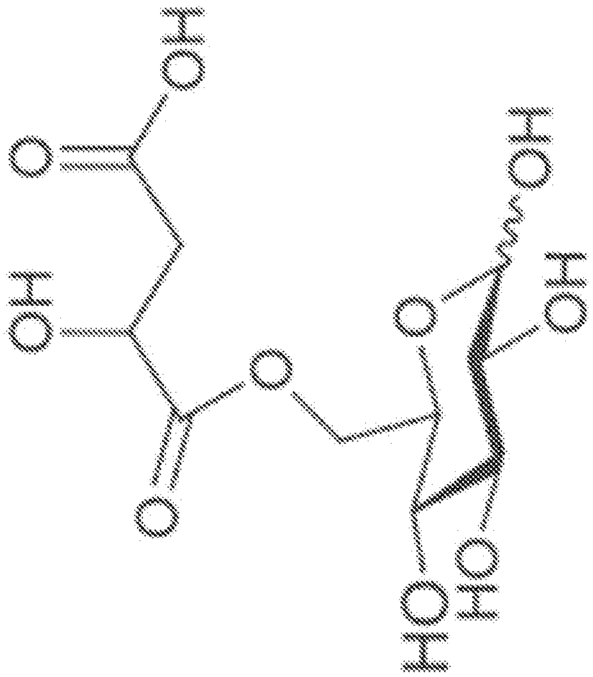
FIG. 2 is a molecular diagram of Veracylglucan A
Figure 3:
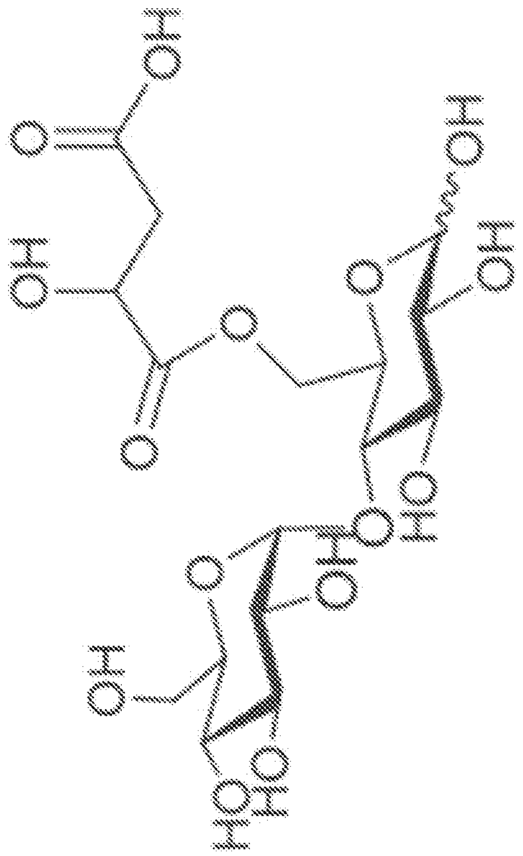
FIG. 3. Is a molecular diagram of Veracylglucan B
Figure 4:
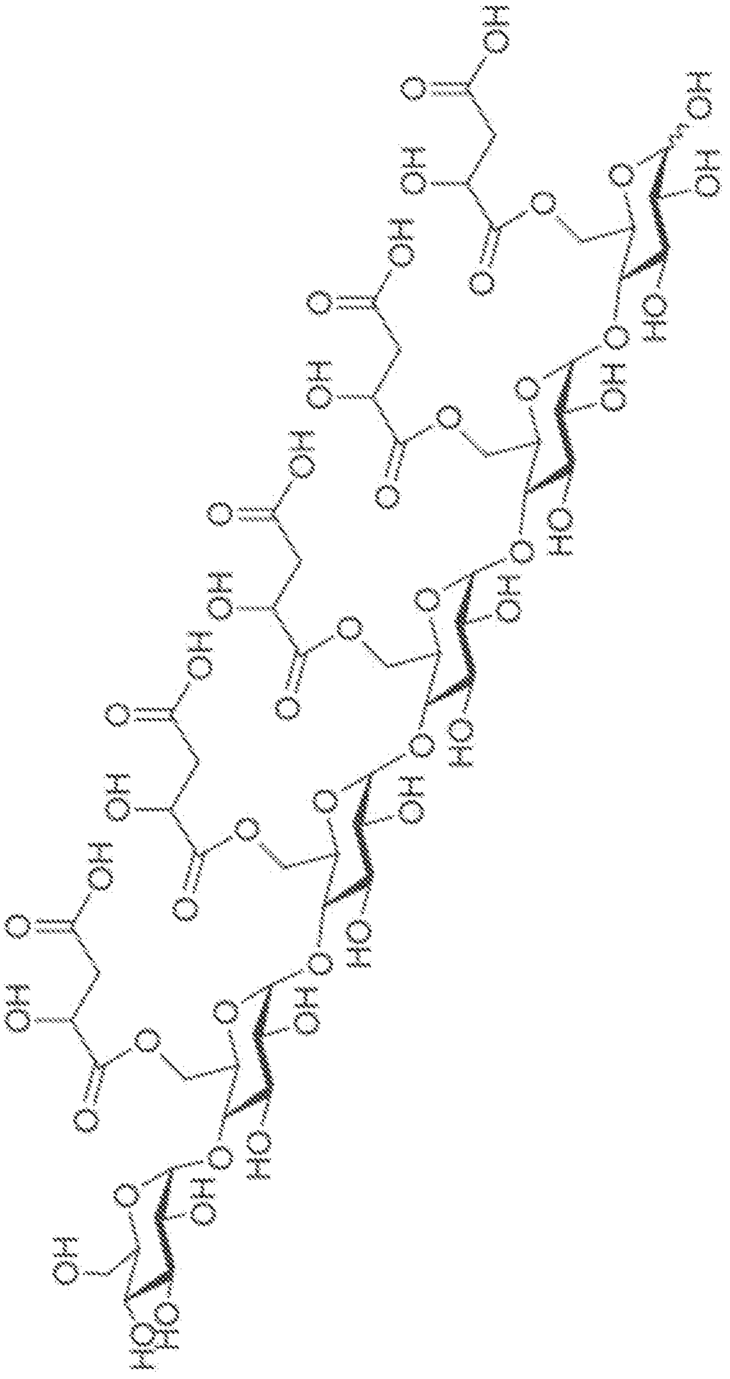
FIG. 4. is a molecular diagram of Veracylglucan C
Figure 5:
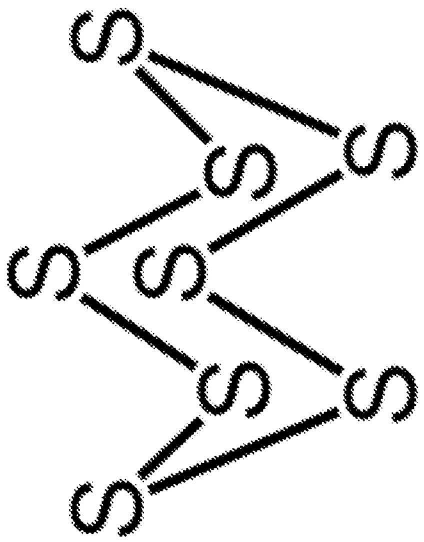
FIG. 5. is a molecular diagram of Sulfur ($S_8$)
Figure 6:
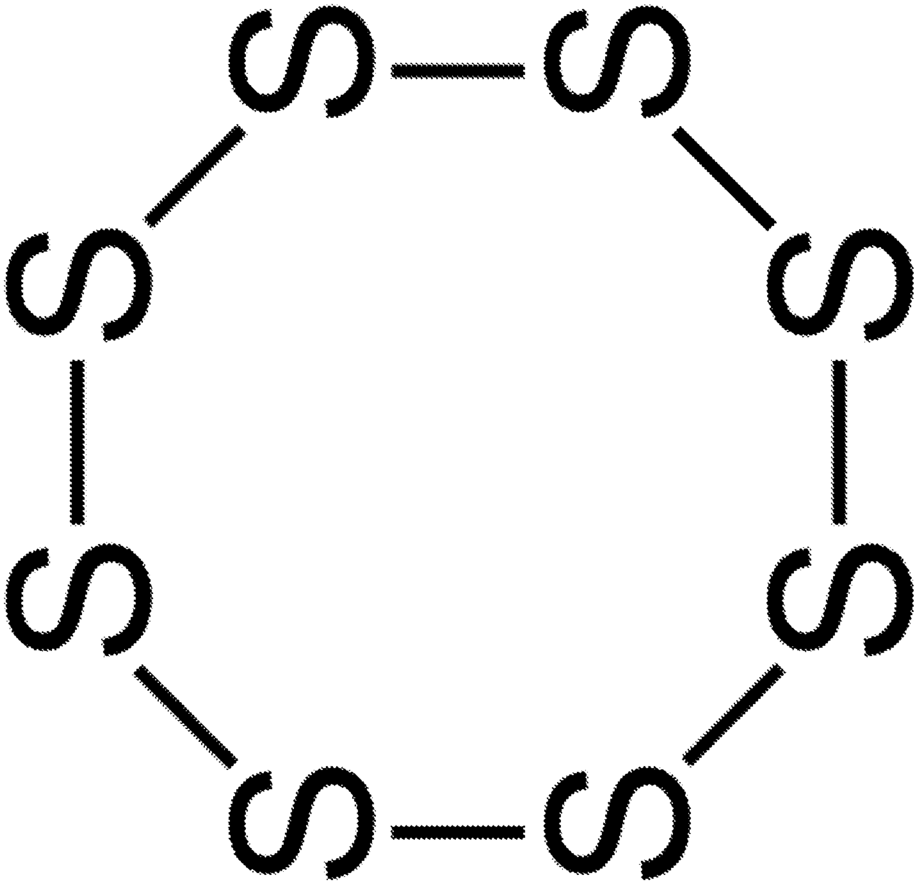
FIG. 6. is a different angle representation of the molecular diagram of Sulfur ($S_8$)

Today there exist many ointments, creams, gels and products for use with animals suffering from various skin ailments. Skin ailments in animals may be caused by a number of skin ailment vectors such as bacteria, fungi, viral infections, dirt, allergic reactions, toxins, and other harmful substances. Worse yet, these skin ailment vectors may be organic or inorganic matter. A plethora of nonprescription treatments exist, but unfortunately, most do not work and are meant for owners of pets to have peace of mind rather than actually relieve pain in an animal. There exist many prescription medications that can clear ailments. However, some of these prescription medications don't work, require a visit to a veterinarian to use, or worse yet, are not dosed properly by the attending veterinarian.

It would be beneficial if there were a simple formula that can treat a majority of skin ailments in various animals. The present disclosure discloses such a treatment. To date there are many products on the market for treating pet skin problems including hot spots but none of them are effective. When owners use the other products on the market, their pets have little to no relief from the symptoms and if there is relief, it does not last long. There is a lack of a substance having minimal ingredients (less than 10) that together, clear up persistent skin issues like hot spots, mange and open wounds.

The present disclosure relates to a topical ointment that is applied daily to an animal's affected area and is used to treat hot spots, mange, sores, open wounds and other related skin ailments.

The present treatment works especially well in cattle, horses, dogs, and other mammals. It can also work in non-mammals such as reptiles and fish. In one embodiment Topical Animal Cream (TPA) is composed of combining Sulfur, *Aloe vera* pulp, and petroleum jelly in various forms and proportions.

Sulfur is a chemical element with the symbol S and atomic number 16. It is abundant, multivalent, and nonmetallic. Under normal conditions, sulfur atoms form cyclic octatomic molecules with a chemical formula $S_8$, as can be seen in figures five and six. Elemental sulfur is a bright yellow, crystalline solid at room temperature. Sulfur belongs to a nonmetallic chemical element (pure product: yellow crystalline solid) under the symbol S. It can actively react with many other elements. It exists in various kinds of forms and compound such as sulfide and sulfate minerals which can be found everywhere around the universe and earth. It is also a key element for all life as the major component of amino acids, vitamins and many other cofactors. Sulfur when mixed with other chemicals and when reacting with chemicals on the surface of a dog also has many antimicrobial and antipathogenic properties.

Sulfur may refer to pure elemental sulfur ($S_8$), or sulfur coming in another form, but associated with other atoms. sulfur is often found bound to other atoms to make compounds such as $Na_2S_8$, $SO_2$, $SO_3$, $H_2SO_3$, $H_2S_2O_7$, $Na_2SO_4$, $SOCl_2$, $S_4N_4$, $P_4S_{10}$, $P_4S_3$. Additionally, different families of sulfur compounds may be utilized such as organosulfur compounds which include, Allicin, (R)-cysteine, Methionine, Diphenyl disulfide, Perfluorooctanesulfonic acid, Dibenzothiophene, and even Penicillin. Other families of organic sulfur compounds that may be used include Thiols, Thioethers, Sulfonium ions, Sulfoxides and sulfones, and Sulfonic acids.

Other forms of sulfur that may be used include Sulfur Colloidal, Azufre10, and regular commercially available sulfur cream. sulfur may also come in the form of common products such as, Liquimat, Sastid Soap, Sulfoam Sulfo-Lo, Sulmasque, Sulpho-Lac, Sul-Ray *Aloe vera* Acne, Thylox Acne, Treatment, Zapzyt Cleansingcream.

Sulfur has found its way into certain cosmetic products. A concentration of above 25% in any product be it pharmaceutical or cosmetic is very uncommon. Some sulfur is found in Acne creams, but the concentration is usually around 5% and not more than 10%. The concentrations listed are by volume or by weight. The reason the concentration of sulfur in other cosmetics and other pharmaceutical products is so low is multifold. First, others in the art have not appreciated that sulfur itself has many antibacterial, anti-inflammatory, and wound healing affects. Generally, when people make creams using *Aloe vera*, sulfur is never included, and inventors focus on the healing properties of *Aloe vera* antibacterial, anti-inflammatory, and enhanced healing effects of *Aloe vera*. However other inventors fail to appreciate that not only does Sulfur itself have healing effects, but it may actually facilitate the healing effects of *Aloe vera* derivative.

The next reason inventors have failed to identify a high concentration of sulfur as effective for treatments is because sulfur may exude a foul odor in high enough concentration. Research has indicated that sulfur and sulfur containing compounds when in high enough concentration may score very highly when measured by an olfactometer [Kasper et al, 2008]. Consumers have also reported that Sulfur has a foul odor when present in high enough concentrations. However, when mixed with TPA the foul odor is greatly reduced if not managed to levels that are undetectable by animals or the human nose. This is because Odorant (or the $S_8$) does not necessarily chemically bond with hydrocarbon polymers found in TPA, but the bonds of the hydrocarbon polymers themselves may prevent Odorant $S_8$ from actually becoming airborne and stimulating an organisms sensory neurons to detect the foul odor of sulfur. The reduction in foul odor is due to the interaction between carbon-carbon and carbon hydrogen bonds with sulfur atoms. Although not a traditional chemical bonding interaction, the bonds between the carbon-carbon and carbon-hydrogen actually prevent sulfur atoms from leaving the complex of TPA.

Third, when cosmetic and other pharmaceutical products have used higher concentrations of sulfur, the sulfur used is not $S_8$, but actually other sulfur containing compounds such as $Na_2S_8$, $SO_2$, $SO_3$, $H_2SO_3$, $H_2S_2O_7$, $Na_2SO_4$, $SOCl_2$, $S_4N_4$. Though such products may be considered to contain "sulfur" because the element sulfur is present, this naming is actually a misnomer. The sulfur in the above compounds has electrons either shared or given up to other atoms, which makes it harder for the sulfur to react with other elements. When sulfur is bound to itself in the $S_8$ form, the individual sulfur atoms can interact with other molecules which have an effect on reducing inflammation, promoting epithelial growth, reducing soars, and healing wounds.

*Aloe vera* is a perennial plant of the Xanthorrhoeaceae family. It is also placed by most sources in the Liliaceae family although it has been designated its own family, known as Aloeaceae. *Aloe vera* has succulent leaves and is widely cultivated around the world. *Aloe* gel consists primarily of water (>98%) and polysaccharides such as pectin, cellulose, hemicellulose, glucomannan, acemannan, and mannose derivatives. *Aloe vera* also contains potentially active constituents, such as vitamins, enzymes (especially amylase), minerals, sugars, lignin, saponins, salicylic acid, and amino acid.

In some instances, if *Aloe* gel is used the other 2% of the *Aloe* gel constituents that are not the actual *Aloe* gel must be removed for 100% pure *Aloe* gel. In other instances, *Aloe* gel that is up to our at least 80% *Aloe* gel may be used.

The *Aloe* leaf can be divided into two major parts, namely the outer green rind, including the vascular bundles, and the inner colorless parenchyma containing the *Aloe* gel. Description of the inner central part of the *Aloe* leaf may sometimes be confusing, due to the different terms that are used interchangeably such as inner pulp, mucilage tissue, mucilaginous gel, mucilaginous jelly, inner gel and leaf parenchyma tissue. Sometimes, the term "pulp" or "parenchyma tissue" refers to the intact fleshy inner part of the leaf including the cell walls and organelles. "Gel" or "mucilage" sometimes refers to the viscous clear liquid within the parenchyma cells. Sometimes the liquid may appear yellow.

The three structural components of the *Aloe vera* pulp are the cell walls, the degenerated organelles and the viscous liquid contained within the cells. These three components of the inner leaf pulp have been shown to be distinctive from each other both in terms of morphology and sugar composition as shown in figure below. The raw pulp of *A. vera* contains approximately 98.5% water, while the mucilage or gel consists of about 99.5% water. The remaining 0.5-1% solid material consists of a range of compounds including water-soluble and fat-soluble vitamins, minerals, enzymes, polysaccharides, phenolic compounds and organic acids.

*Aloe vera* pulp may be obtained through commercial means or grinding and straining the *Aloe vera* plant. In other forms, *Aloe* from the plant may be combined with plant material (including *Aloe vera* plant) and the pulp derived from there. Additionally, at times *Aloe vera* pulp may be combined with other chemicals including alcohols, stabilizers, surfactants, salts, acids, sugars, enzymes, impurities, and other chemicals not naturally occurring or naturally occurring to the *Aloe vera* plant. The inclusion of these additional chemicals into the TPA, will not affect its efficacy, however in certain instances it may be favorable not to include these additional chemicals. Additionally, there are many *Aloe vera* pulp beverages that may also be combined and work to form TPA. Additionally, sometimes it is best to keep impurities below 5% by weight of the final solution. Sometimes it is best to have no more than 1 g of impurities.

In some instances, *Aloe vera* derivative, *Aloe vera* constituent, and *Aloe vera* may be used interchangeably. In other instances, *Aloe vera* may refer to *Aloe vera* gel. *Aloe vera* may also refer to *Aloe vera* constituent. *Aloe vera* derivatives and *Aloe vera* itself may be used. One *Aloe vera* derivative is Acemannan ($C_{66}H_{10}1NO_{49}$). Acemannan has an IUPAC name of Methyl 3-O-acetyl-4-O-methyl-α-D-mannopyranosyl-(1→4)-3-O-acetyl-α-D-mannopyranosyl-(1→4)-3-O-acetyl-α-D-mannopyranuronosyl-(1→4)-3-O-acetyl-α-D-mannopyranosyl-(1→4)-2-acetamido-2-deoxy-α-D-mannopyranosyl-(1→4)-3-O-acetyl-α-D-mannopyranosyl-(1→4)-3-O-acetyl-α-D-mannopyranosyl-(1→4)-3-O-acetyl-α-D-mannopyranoside. Acemannan may sometimes replace *Aloe vera* entirely when making TPA. In other instances, a certain dry weight percentage of Acemannan must be found in the final product of TPA. In one embodiment 0.001-1% Acemannan by dry weight must be found in the final TPA for the TPA to be effective.

Veracylglucan is another *Aloe* derivative found in *Aloe vera*. One particularly potent form for TPA is Veracylglucan C (C56H82O51). Veracylglucan C has an IUPAC name of (3S)-4-{[(2R,3S,4R,5R,6R)-3-{[(2R,3R,4R,5S,6R)-6-({[(2S)-3-carboxy-2-hydroxypropanoyl]oxy}methyl)-3,4-dihydroxy-5-{[(2R,3R,4S,5S,6R)-3,4,5-trihydroxy-6-(hydroxymethyl)oxan-2-yl]oxy}oxan-2-yl]oxy}-6-{[(2R,3S,4R,5R,6R)-2-({[(2S)-3-carboxy-2-hydroxypropanoyl]oxy}methyl)-6-{[(2R,3S,4R,5R,6R)-2-({[(2S)-3-carboxy-2-hydroxypropanoyl]oxy}methyl)-6-{[(2R,3S,4R,5R)-2-({[(2S)-3-carboxy-2-hydroxypropanoyl]oxy}methyl)-4,5,6-trihydroxyoxan-3-yl]oxy}-4,5-dihydroxyoxan-3-yl]oxy}-4,5-dihydroxyoxan-3-yl]oxy}-4,5-dihydroxyoxan-2-yl]methoxy{-3-hydroxy-4-oxobutanoic acid. Veracylglucan is found in many *Aloe vera* plants. Some plant *Aloe* plants contain Veracylglucan C in less concentration when compared to Veracylglucan A and B. When Veracylglucan C is at a lower concentration, or a lower concentration when compared to Veracylglucan A and B, better wound healing results may be obtained.

Veracylglucan may sometimes replace *Aloe vera* entirely when making TPA. In other instances, a certain dry weight percentage of Veracylglucan must be found in the final product of TPA. In one embodiment 0.001-1% Veracylglucan by dry weight must be found in the final TPA for the TPA to be effective. Other researchers have indicated that Veracylglucan A and Veracylglucan B have different or even better healing results when used in other jells or on their own. In the experience of the inventors this is false. When using an *Aloe vera* derivative with a higher proportion of Veracylglucan C better healing results have been obtained. More so, when Veracylglucan A and Veracylglucan B are removed from TPA entirely, to only leave Veracylglucan C in the final TPA better results are obtained. In one embodiment 0.001-1.5% Veracylglucan B by dry weight must be found in the final TPA for the TPA to be effective.

The Enzyme amylase is present in every *Aloe vera* producing plant. *Aloe vera* containing high levels of amylase has been found to provide better wound healing properties for TPA. Interestingly enough, the amylase may be denatured and still make the TPA effective. The following protein sequences for amylase are effective when added to TPA.

Sequence ID 1

MPVDHGAHDALDDLLAGRHPDPFHILGPHADGPRSWVRVLVPNAEQVTVLLGAKDEE

WPLTHVRHGMYSGLVDGLAPGQPTAYRLRIKWPTGEQITEDPYAFSALLGDLDLHLISE

GRHEYLADCLGSHVMDVEGVRGVRFAVWAPNARRVSVVGDFNSWDGRRHPMRLRHS

AGVWEIFIPRLQAGTRYKYEIAGPEGQLLPLKADPLARQTEAPPATASIVPDPTPYTWTD

DDWMATRAARQAQDAPITVYEVHAGSWLPRDGEDDGECVWRRLATRLVPYARDLGF

THLELMPIMEHPFGGSWGYQPLGVFAPTARYGTPRDFAAFVDACHAAGLAVILDWVPA

HFPTDTHGLSHFDGTALYEYQDPREGFHPDWNTLIYNLGRTEVHNFMVASALEWVRRY

HIDGLRVDAVASMLYRDYSRAAGEWIPNRYGGRENLEAVDFLRDMNATVHRLCPGAIT

VAEESTAWPGVSARTEDGGLGFSYKWNMGWMHDTLRYMHNDPVHRRYHHNDMTFG

MVYAYSERFILPLSHDEVVHGKGSLLNKMPGDRWQRHANLRAYFGFMWGHPGKKLLF

MGGEIAQEREWNHDASLDWGALDDGLHRGVQKLVRDLNHVYAELPALHRHDHDASG

FEWLIGDDYANSVYAFVRRDGDALALVVCNFTPVPRDGYRIGVPRAGRWRERINTDAG

DYGGSGMGNSGGRHTEAVAAHGREQSLVLTLPPLATLIFQFEG

Sequence ID 2

MRIYYVHPLHVGSLSGDSFSHWQARCARIKSLGFDTLMTAPLWAPDPAGNPYVPDDPD

RLHPALGDMDLAAAMTALSRLCGEHGLALMIDLPLEKVAIDGAAARAHPHWYEDAGG

DALLDPRRPWEDRHALPLRREHGRAPAGFVDHWIERLGLWVENGVAGFRCEGLAQLA

PADWRDLIQGVRAVRPDCRWLAWTPGVAPWDVAPLAGVGFDGVFSSFPWWDYRAEW

LLEETDRLRAIAPVIAPVEAPYAKRVASWRSDPAGRYRNAARAVWTAAVVGDGVLVP

MGFEDAATHALERDGSGVREDPQGDPGLHIDIGRANQWLARTASARGPLHSLQGPHTG

VTALFRGDGAATPAAGAGRGSARLIVLNPSDDVAASPDWDALRARLPDGYGRLDQWD

ADRPAQDLPTTLAPGDMLRLGASRLPPVTVPASDDTRLGVTAAMRQPRLAIEHVTPAV

DDGAFPIKRIAGETITVEADVFCDGHEYIAVALLWRAADDKEWQRVPMTPLGNDRWTA

SFAPARIGRHYYAVQGWDDAWTTFRDGLEKKYRAGVDIALETAEGRGLVQEALERLPD

TAETSAAALRQVLRVLGAAPAEKPRRDRKKSAGEASPPRFPSPTPDQVAALLDAATARA

MREADDRRFETTSAIYPVTVDRPAAIFSSWYEIFPRSQSGDPRRHGTFDDVIATLPRVRA

MGFDTLYFPPIHPIGARNRKGRNNSLQAGPDDPGSPYAIGSEDGGHDALHPQLGTLDDF

RRLVAAARAHGLELALDFAIQCSPDHPWLKAHPEWFDWRPDGSLKYAENPPKKYEDIV

NVDFYGAKPGASRQAPLWRALRDVVLFWVAQGVRVFRVDNPHTKPLPFWEWMIGDV

QGRHPDVLFLSEAFTRPKMMYRLAKVGFSQSYTYFTWRETKQEFTEYLTELTQGPPADF

FRPHFFVNTPDINPRFLQQSGRGGFLIRAALAATLSGLWGVYNGFELCEASAVPGKEEYL

DSEKYEIRAWDHERPGNIVREITRLNAIRRANPALHTHLGVRWHTAWDDQVLFFSKSTP

QRDNVLLVAISLDPHHPRDVVLEIPMWEFGLPDDGPLQAEDLIDGNRMVWRGKQQGVH

LHPDQPYRIWRVTPA

-continued

Sequence ID 3
MTASVPAVSYSHGAVRQAGGRTRFRLWAPNANDGVVLEIAGHEPLPMRVVADGYYEI

DADCEPGARYRYRVAPDLAVPDPASRLQAGDVHDDSVVVDGGDAYAWRHPDWRGRP

WTETVLYEVHPGLAGGYAGIEQRLPELAALGITAIELMPIADFPGPRNWGYDGVLPYAP

DRAYGDPDELRRLIDTAHGLGMMVFLDVVYNHFGPDGNYLNAYAADFFRQDLQTPWG

AAIDFRRPQVRRYFAENALYWLAEYRFDGLRLDAVHAIRDVGWLEEMAAFVRAHIDPG

RHVHLVLENDDNQVHPLLHGYQAQWNDDAHHVLHHLLTGESEGYYEDYVEQPAQRL

ARALTEGFVYQGQPSRHRGGQRRGERSDLLPPTAFVFFLQNHDQTGNRALGERLGPLLR

DARILKAATALQLLTPQIPLIFMGEERGATTPFLYFTSHADPQLATAVRDGRRKEFQHFR

AFANPAMRERIPDPNDPATYANANPFTGEPDADTLATYTELLAVRRREIVPRLQGAHAL

GAHVLGLRAVVAQWRMGDGATLTLYANLGGVDLRPDWLQVDLADQAVVYESETGA

GAALHEGLLWRGCTIALLQAPVAGARMTTDTKEYP.

Sequence ID 4
MARQATGRAPAPRPAVPHLASDARLNAQPGRVPRPAQRQEDNGMSDNHVNSPNRDDP

LWYKDAVIYQLHVKSFFDANNDGVGDFAGLVEKLDYIASLGVNTIWLLPFYPSPRRDD

GYDIAEYRGVHPDYGTLAGVRKLIKAAHARGLRVITELVVNHTSDQHPWFQRARRAKP

GSAARNYYVWSDNDQAYAGTRIIFLDTEKSNWTWDPVAGAYFWHRFYSHQPDLNYDN

PQVLKEVIGVMRFWLDLGVDGLRLDAVPYLVEREGTNNENLPETHAVLKKIRAQLDAE

YPGRMLLAEANQWPEDAQEYFGQGDECHMSFHFPLMPRMYMAIAREDRFPITDIMRQT

PDIPETCQWAIFLRNHDELTLEMVTSNERDYLWNTYAADRRARINLGIRRRLAPLMERD

RRRIELMNSLLLSMPGTPVIYYGDELGMGDNIHLGDRDGVRTPMQWSPDRNGGFSRAD

PERLPLPPLMGPLYGYEAVNVEAQQRDPHSLLNWSRRMLATRAKTQAFGRGTLRFLFP

GNRNILAYLREYEATTILCVANLSRASQPVELDLSSLAGRVPVELLGGTPFPAIGELTYLL

TLPPYGFYWFDLSASASPPEWHATHPERMPEYYTLVLRGRTGYELTEGAVRSLREDVLP

LYLSRQRWYPKDRKVKMAQAAYAAQLPGADHECFIAEIQVDFDGKPARFLLPAALIWD

ETLPPMAQQYALARVRRAAEMGYLTDAFTLPSFIHALVRGLRERTEIPVPRAHPPAVLRF

RGEPTLDKIELPPDAEVQWFTGEQSNSSVTLGGIMMLKLLRRIVPGVHPEAEMTRRLTEV

GYANGAPLLGEIQRIDEDGTPHTLALMHQMITNQGDAWTWTLNYLKRTLEAAALTAES

AEDYDEDLLGYINFAHTMGKRLGELHAALSLPTDDAAFKPHRATRHDAERRAKAVIAM

LDQGLDTLKANMGRLDAAHAETAAWLAEHRDALVEVVRDLAANEEDTLHIRIHGDFH

LGQVLAAQGDAYLIDFEGEPARTLEERRAKTSALRDVAGLLRSFDYAAATLADGTGKG

KGKAEETGEAQIAEQQLRTRRQDLIERFRVTAGESFLAGYREVAHTTEHPWITPEVEAPL

IDLALIEKAAYEVRYEAAHRPDWVGIPLAGLASLAARLLSDGSAASSHP.

Sequence ID 5
MPNQPRITEGSPFPLGATLDDDGVNFALFSAHATKVELCLFDELGEQETERIVLPEFTDEI

WHVHVAGLNAGTVYGYRVHGPYEPENGHRFNPNKLLLDPYAKAYVGELKWDPAVFG

YPIGDEQADLGFDERDSAAFVPKCRVVDQRFTWTHATRVRVPWERTIFYETHVRGYTM

RHPAVPEALRGSFAGLARDAVIDHIKSLGVTSVELLPIHAFVNDSHLLEQGLTNYWGYN

TIGFFAPDPRYFSQVPGAITELKQMIDRFHEAGLEIILDVVYNHTAEGSELGPTLSFRGIDN

ASYYRLLPDQKRYYINDTGTGNTLNLSHPRVLQMVMDSLRYWVTEMKVDGFRFDLATI

LAREPDGFDYNSGFLKACRQDPILSSVKLIAEPWDCGPGGYQVGNFPPGWAEWNDRYR

DTVRAFWKGDEGMAPELAGRITGSGGDFNHGGRRPWASVNFLTAHDGYTLNDLVSYN

-continued

DKHNEANGEDNRDGHSDNRSWNCGAEGPTDDPDIRALRERQKRNMLATLLFSQGTPMI
VAGDEFGRTQQGNNNAYCQDNEISWVDWEINEDGAALIEFLRKLTTLRHTLPVLRRGRF
LTGDYDESMDVADVKWLSSSGEALTPEQWADTNMRCFGLIIDGRARATGIRRPASDAT
LLLIFNAYHDVVDFTLPEIPGNDRWTCLIDTNAPVRAELPQFASGDVYQVTGRSLLLFSL
QAKGPTQRVFDKLEEALTDEETPEPAREAAAIVKKSVKKEKPSK.

Sequence ID 6

MPNQPRITEGSPFPLGATLDDDGVNFALFSAHATKVELCLFDELGEQETERIVLPEFTDEI
WHVHVAGLNAGTVYGYRVHGPYEPENGHRFNPNKLLLDPYAKAYVGELKWDPAVFG
YPIGDEQADLGFDERDSAAFVPKCRVVDQRFTWTHATRVRVPWERTIFYETHVRGYTM
RHPAVPEALRGSFAGLARDAVIDHIKSLGVTSVELLPIHAFVNDSHLLEQGLTNYWGYN
TIGFFAPDPRYFSQVPGAITELKQMIDRFHEAGLEIILDVVYNHTAEGSELGPTLSFRGIDN
ASYYRLLPDQKRYYINDTGTGNTLNLSHPRVLQMVMDSLRYWVTEMKVDGFRFDLATI
LAREPDGFDYNSGFLKACRQDPILSSVKLIAEPWDCGPGGYQVGNFPPGWAEWNDRYR
DTVRAFWKGDEGMAPELAGRITGSGGDFNHGGRRPWASVNFLTAHDGYTLNDLVSYN
DKHNEANGEDNRDGHSDNRSWNCGAEGPTDDPDIRALRERQKRNMLATLLFSQGTPMI
VAGDEFGRTQQGNNNAYCQDNEISWVDWEINEDGAALIEFLRKLTTLRHTLPVLRRGRF
LTGDYDESMDVADVKWLSSSGEALTPEQWADTNMRCFGLIIDGRARATGIRRPASDAT
LLLIFNAYHDVVDFTLPEIPGNDRWTCLIDTNAPVRAELPQFASGDVYQVTGRSLLLFSL
QAKGPTQRVFDKIEEAITDEETPEPAREAAAIVKKSVKKEKPSK.

Dry *Aloe vera* or *Aloe vera* powder may also be used instead of regular gelatin *Aloe vera* or *Aloe vera* gel. There are multiple ways to make and types of dry *Aloe vera*. For Dry *Aloe vera* to work in any of the embodiments it must contains no more than 5% liquid water by weight. Note that when combined with other constituents such as hydrocarbons, sulfur, or petroleum jelly, liquid may be added to the entire TPA solution. This extra liquid however will not have an effect on the efficacy of the TPA.

In the experience of the inventors the best form of dried *Aloe vera* or *Aloe vera* powder may be produced by the following. First a specimen *Aloe vera* plant leaf is selected. So long as the leaf does not have blight or is rotten, all specimens will work. Next the plant should be washed in warm water. After washing the outer layer of the leaf (sometimes referred to as the rind) the rind should peeled away. The rind in most species of *Aloe vera* will be thick and green. Once the rind has been removed the specimen should be washed again. When washing a second time, a technician may notice yellow liquid exuding from the specimen. This yellow liquid contains many *Aloe vera* constituents, some of which sequester potassium when ingested. At this step a technician should be sure to wash their hands to prevent ingestion of the liquid for undesired effects.

The specimen may then be cut up into smaller pieces to make handling and desiccation easier. Whatever technique is used to cut up the specimen, the end specimen pieces should be of uniform size and shape to ensure even drying. Next the specimen pieces may be placed on trays or a flat surface and put into a desiccator. The desiccator should be turned to 135° F. degrees but not more than 200° F. In the experience of the inventors, 140° F. degrees works well.

Next the specimen should be desiccated for at least 12 hours. In the experience of the inventors no more than 50-56 hours has even been needed to desiccate a batch of cut up specimen. Desiccation times are mainly increased based on the liquid content of the specimens. Specimens with high liquid content will take longer to desiccate than specimens with smaller amounts. One the pieces have been fully dehydrated they need to be broken down further to create a fine powder. This may be accomplished with a mortar and pestle or conventional food processor. Once broken down into a fine powder, the dried *Aloe vera* may be dedicated further to reduce the liquid content of the final fine *Aloe vera* Powder product.

In some embodiments, the *Aloe vera* present in TPA may actually be formed from a 50%, 50% combination of wet *Aloe vera* gel and dried and rehydrated *Aloe vera* dust. A potential formulation for such formulation of TPA includes *Aloe vera* wherein the *Aloe vera* derivative may be selected from a group consisting of *Aloe vera* gel, *Aloe vera* powder *Aloe vera* extract, Veracylglucan ($_{c56}H_{82}O_{51}$), Acemannan $C_{66}H_{10}1NO_{49}$; wherein the hydrocarbon polymer may be selected from the group consisting of petroleum jelly hydrogenated castor oil and beeswax. Another potential formulation includes 30%-33% by weight sulfur; 30%-33% by weight *Aloe vera* or *Aloe vera* derivative; 30-33% hydrocarbon polymer; at most 5% impurities. In other embodiments TPA may be made from ⅓ hydrocarbon polymer, ⅓ sulfur, ⅓ *Aloe vera.*

Another formulation includes the topical treatment above wherein the *Aloe vera* or *Aloe vera* derivative further comprises at least 30 micrograms of Veracylglucan, at least 10 micrograms of Acemannan, and 30 grams of *Aloe vera* plant extract. Another treatment includes the topical treatment above wherein the *Aloe vera* or *Aloe vera* derivative is obtained from a plant species within the *Aloe* family, the plant further comprising *Aloe vera, Aloe viridiflora, Aloe*

*excelsa, Aloe thraskii*, and *Aloe namibensis*. Another treatment may include an impurities, the impurities further comprise amylase selected from the SEQUENCE ID 1, SEQUENCE ID 2, SEQUENCE ID 3, SEQUENCE ID 4, SEQUENCE ID 5, or SEQUENCE ID 6. The impurities may contain other chemicals or molecules besides amylase as well as amylase.

The specimen should then be dehydrated. To dehydrate the specimen, the specimen should be placed in a dry area and exposed to warmth for a week. If an oven is used, the oven should be heated to 200 degrees and the *Aloe vera* left there for 2-3 days. A desiccator may also be used to speed up the specimen drying process. Inserting the specimen into a dehydrating machine may comprise 135° F.-200° F. for six hours. It could also comprise inserting the specimen into a dehydrating machine may comprise 135° F.-200° F. for four.

The following *Aloe vera* derivatives have been found in and may be used in TPA. *Aloe*-emodin, aloetic-acid, anthranol, aloin A and B (or collectively known as barbaloin), isobarbaloin, emodin, ester of cinnamic acid Pure mannan, acetylated mannan, acetylated glucomannan, glucogalactomannan, galactan, galactogalacturan, arabinogalactan, galactoglucoarabinomannan, pectic substance, xylan, cellulose 8-C-glucosyl-(2'-O-cinnamoyl)-7-O-methylaloediol A, 8-C-glucosyl-(S)-aloesol, 8-C-glucosyl-7-O-methyl-(S)-aloesol, 8-C-glucosyl-7-O-methyl-aloediol, 8-C-glucosyl-noreugenin, isoaloeresin D, isorabaichromone, neoaloesin A, Alkaline phosphatase, amylase, carboxypeptidase, catalase, cyclooxidase, cyclooxygenase, lipase, oxidase, phosphoenolpyruvate carboxylase, superoxide dismutase, Calcium, chlorine, chromium, copper, iron, magnesium, manganese, potassium, phosphorous, sodium, zinc, Arachidonic acid, γ-linolenic acid, steroids (campestrol, cholesterol, β-sitosterol), triglicerides, triterpenoid, gibberillin, lignins, potassium sorbate, salicylic acid, uric acid.

The following amino acids, proteins, Saccharides and Vitamins have also been found in *Aloe vera* and may be used in TPA. Alanine, arginine, aspartic acid, glutamic acid, glycine, histidine, hydroxyproline, isoleucine, leucine, lysine, methionine, phenylalanine, proline, threonine, tyrosine, valine, Lectin, Mannose, glucose, L-rhamnose, aldopentose, B1, B2, B6, C, β-carotene, choline, folic acid, α-tocopherol.

Some *Aloe vera* pulp may contain trace amounts of calcium, copper, chromium, sodium, selenium, magnesium, potassium, manganese, zinc, and Vitamin B-12. *Aloe vera* pulp with these trace chemicals may be used and may actually be preferred.

In some instances *Aloe vera* with trace amounts of other constituents may actually be preferred to regular pure *Aloe vera*. For example *Aloe vera* with enriched Vitamin B-12 may actually facilitate healing better than a formulation made with regular *Aloe vera*. In some instances when Vitamin B-12 is enriched it should be enriched so the concentration of B-12 in the final TPA is between 0.006 micrograms and 6 micrograms per liter of TPA. In other instances, the concentration of TPA in should be 0.006-0.009 micrograms per liter of TPA.

In certain instances, *Aloe vera* pulp from individual strains of plants may be used. Strains may be selected based in part on their tendency to produce or overproduce certain chemicals. All strains fall within the *Aloe* genus of plants. These chemicals include, Anthraquinone, Aloin, Mannose, Acemannan, *Aloe* emodin, Emodin, Glucomannan, Anthrone, beta-Sitosterol, Chromone, Lupeol, Mannan, Streptozotocin, Arabinogalactan, Silver sulfadiazine, Sulfadiazine, Myristic acid, Allantoin, Polyethylene glycol, Alloxan. In other instances, a strain that under produces, or produces none of the above identified chemicals may also be selected for. For example a strain of *Aloe vera* that does not produce any Alloxan, or very little (0.001-10 μg of Alloxan per plant) of Alloxan may also be used for *Aloe vera* pulp.

*Aloe vera* sometimes refers to the specific genus and species of plants in the *Aloe* genus. *Aloe vera* derivatives, and plants that may also be referred to as *Aloe vera*, may also refer to plants within this genus including, *Aloe aculeata, Aloe Africana, Aloe albida, Aloe albiflora, Aloe arborescens, Aloe arenicola, Aloe argenticauda, Aloe bakeri, Aloe ballii, Aloe ballyi, Aloe brevifolia, Aloe broomii, Aloe buettneri, Aloe camperi, Aloe capitata, Aloe comosa, Aloe cooperi, Aloe corallin, Aloe dewinteri, Aloe erinacea, Aloe excelsa, Aloe ferox, Aloe forbesii, Aloe helenae, Aloe hereroensis, Aloe inermis, Aloe inyangensis, Aloe jawiyon, Aloe jucunda, Aloe khamiesensis, Aloe kilifiensis, Aloe maculata, Aloe marlothii, Aloe mubendiensis, Aloe namibensis, Aloe nyeriensis, Aloe pearsonii, Aloe peglerae, Aloe perfoliate, Aloe perryi, Aloe petricola, Aloe polyphylla, Aloe rauhii, Aloe reynoldsii, Aloe scobinifolia, Aloe sinkatana, Aloe squarrosa, Aloe striata, Aloe succotrina, Aloe suzannae, Aloe thraskii, Aloe vera, Aloe viridiflora, Aloe wildii.*

In the experience of the inventor, the particular species *Aloe vera, Aloe viridiflora, Aloe excelsa, Aloe thraskii*, and *Aloe namibensis* produce an *Aloe vera, Aloe vera* derivative, impurities, or *Aloe vera* powder that not only enhances the healing of TPA, but also make all constituents of the TPA bind together more effectively than other plants within the *Aloe* genus.

Petroleum jelly is petrolatum, a hydrocarbon, $C_{15}H_{15}N$, (1,1,2-Trimethylbenzeindole) with a boiling point of 322° C. (610° F.) and a melting point between 70 and 80° C. (160 and 175° F.). It is flammable only when heated to liquid; then the fumes will light, not the liquid itself, so a wick material like leaves, bark, or small twigs is needed to ignite petroleum jelly. It is colorless or has a pale yellow color (when not highly distilled), translucent, and devoid of taste and smell when pure. It does not oxidize on exposure to the air and is not readily acted on by chemical reagents. It is insoluble in water. It is soluble in dichloromethane, chloroform, benzene, diethyl ether, carbon disulfide and oil of turpentine. Petroleum jelly may also be replaced with hydrogenated castor oil and/or beeswax. In some embodiments a Petroleum jelly, hydrogenated castor oil, and beeswax mix may be preferable to just petroleum jelly.

Petroleum jelly should only be used externally and not ingested. Although appropriate to put on a wound, even open soars, having Petroleum jelly enter the bloodstream and is not ideal. Additionally, petroleum jelly may be mixed with other hydrocarbons not conventionally found in Petroleum jelly such as glycerol, triglycerides, and esters. It should be appreciated that there are different brands of Petroleum jelly on the market, and that although the main chemical formula is the same, sometimes chemicals may be added to the petroleum jelly compositions. These additives do not usually have an effect on the efficacy of the TPA.

TPA is formed by mixing various versions of Sulfur, *Aloe vera* pulp, and petroleum jelly. In some forms of TPA, mixing sulfur powder, the pulp of the *Aloe vera* (fresh or freeze dried or *Aloe vera* powder) and petroleum jelly in equal parts yields effective TPA. Some forms of TPA are more effective if the *Aloe vera* pulp is fresh. Fresh can mean used within 24 hours or up to two weeks. If the *Aloe vera* is freeze dried or dehydrated then the mixture requires one part sulfur, one part petroleum jelly and ¼ part *Aloe vera*. The other part may be other chemicals or more sulfur and petroleum jelly. Once the Sulfur, *Aloe vera* pulp, and Petroleum jelly have been mixed, an ointment should be obtained.

Other effective formulations of TPA include 30% sulfur, 30% *Aloe vera* pulp, 30% Petroleum jelly, 10% water with additives. The other 10% may also constitute alcohol, glycerol, or cosmetic products. Additives to water include chemicals besides water. These chemicals may further include elemental chemicals such as carbon, or compounds. Other effective formulations include 25% Sulfur 25% *Aloe vera* pulp and 50% Petroleum jelly. 25% Sulfur 50% *Aloe vera* pulp and 25% Petroleum Jelly.

Other appropriate combinations include at least 30 grams of *Aloe vera*, at least 30 grams of petroleum jelly, and at least 30 grams of sulfur. At least 30 grams of *Aloe vera*, at least 30 grams of petroleum jelly, and at least 30 grams of sulfur and not more than one gram of impurities and/or other constituents. 30 grams of *Aloe vera*, at least 30 grams of petroleum jelly, and at least 30 grams of sulfur. 30 grams of Veracylglucan, 30 grams of petroleum jelly, 30 grams of solid powder form $S_8$. 30 grams of Acemannan, 30 grams of petroleum jelly, and 30 grams of Sulfur. 30 milligrams of Veracylglucan, 10 milligrams of Acemannan, and 30 grams of *Aloe vera* plant extract, 30 grams of petroleum jelly, and 30 grams of sulfur.

The TPA may also be combined with other ointment agents that make the TPA appear to be more like ointment and increase its efficacy. Appropriate ointment agents include Squalane, Pentahydrosqualane, Liquid paraffin, mineral oil, Polyisobutene, Paraffin, and waxes. TPA may also come in non-ointment forms such as aerosol sprays, dusts, roll-on bars, or gels.

To effectively apply the TPA on an animal, an animal's affected area should be cleaned. An affected area is any party of the animal's skin or body that is irritated or infected. Types of irritations or infections include, ulcers, hot spots, red spots, infections, allergic reactions, cuts, bruises, welts, goiters, growths, or any part of the skin that is not maintaining normal homeostatic function. In other instances, an affected area can be a range of healthy and diseased tissue such as mumps and growths. If heavy mud or debris is present near a wound, the heavy mud and debris should be removed. Mud may be washed away with warm water, no soap. It should be noted that cleaning the area may disturb the animal's natural oils and secretions present in their skin and can further exasperate the skin issue. It should be noted that the cleaning should not disturb the animals' natural oils or secretions.

The TPA should then be applied to the wound site. This may be accomplished by rubbing the TPA into the animals wound and surrounding skin. In the experience of the inventors applying a bandage or wrapping material around the wound may prevent an animal from scratching. In most cases however, such wrapping is unneeded because the healing properties of TPA prevents the animal from continuing to attack the wound. The TPA may either be reapplied twice a day or every 4 hours as needed. In some instances, animal caretakers may wish to apply the TPA once a day for two weeks (fourteen days). In other instances, animal caretakers may wish to apply the TPA twice a day for fourteen days. Sometimes applying TPA 3-4 times a week for two weeks is sufficient.

TPA is especially effective against cuts. A cut is defined as a skin lesion in which the natural connectivity of epithelial tissue has been disturbed by an abrasion. TPA promotes epithelial cell growth. In the experience of the inventors, effective directions on how to use TPA include: cleaning the affected area if mud is present, and applying a thick layer of TPA to the affected area once a day for seven to twenty one days depending on the severity of the skin problem. If the animal is an indoor animal, you should cover the medicine with a t-shirt or bandage, so the medicine doesn't get everywhere. It is also important not to bathe the animal for a duration of the treatment. A slight bath may be permissible if the animal is muddy, but baths should be avoided for a duration of the treatment. Additionally, along with the cessation of medicated shampoos; over the counter shampoos and other topical treatments should be ceased during a duration of the treatment. TPA may be distributed in 4-84 oz containers and stored at 60° F.-86° F. (15° C.-30° C.). TPA is appropriate for most animals but is especially effective with dogs, cats, cattle, horses, and other livestock.

In other instances, if the affected area contains thick and long fur, the area should be sheared before the TPA is applied to ensure direct application on the affected area. Application of the TPA can occur in many ways. For one, the TPA may simply be slathered on the affected area. Other times a bandage or piece of cloth may be impregnated with the TPA, the bandage or piece of cloth introduced to the affected area. Treatments with cloth or band aids is often helpful to animals because the TPA may rub off and be less effective if not covered by something as the animal moves. Again, in certain instances, an animal's fur or epidural covering may need to be removed (for example shaved) for higher efficacy when the TPA is applied. In other instances, the TPA will retain its efficacy when applied directly on the fur, but to an affected area. At any rate the TPA should be thoroughly mixed, and the TPA generously applied to the animal's affected area of skin.

Before using TPA, it is important to check if an animal has already been prescribed or is already using medications. In most instances, if an animal is on a medication regime, the regime should be ceased before and during the use of TPA. In other instances, the use of TPA with a medicine regime need not be stopped Animals on blood thinners or diagnosed with other heart medications might not be recommended for TPA. An animal's veterinarian or healthcare provider should be consulted if they have one of the above conditions before TPA is used.

TPA may also be combined with other chemicals to make the final composition more effective. For example the sulfur, *Aloe*, Petroleum jelly, may be combined with various other cosmetic products. For example TPA may be combined with Allantoin, *Bacillus* Ferment, Ceramide 3, Emu Oil, *Euphorbia cerifera* (Candelilla) Wax, Glyceryl Behenate, Hydrogenated Castor Oil, Lysine HCl, *Melaleuca alternifolia* (Tea Tree) Leaf Oil, *Olea Europaea* Fruit Oil, Phytosphingosine, Silver Citrate, Squalane, Tocopheryl Acetate, Tribehenin, Vegetable Oil.

A study was conducted to evaluate the effectiveness of TPA when applied to dogs. Dogs of various species, weights, sizes, health, and who may have at some point participated in other medical regimes (taking antibiotics, flea medication, mange medication). The study followed eleven test subjects as TPA was applied to various lacerations the subjects had. 90.9% of test subjects in the study experienced wound reduction. Wound reduction was characterized by handler reporting and photographic evidence of the wounds recorded before application of TPA and for various days after the application. Furthermore, percentage wound reduction was also measured within a margin of +−5% wound coverage. This means that a wound measured to have healed at 80% may be within 75%-85% healed.

63% reported healing of wounds within 90% within fourteen days of use. 27% reported 100% reduction in wound meaning full healing. Another 9% reported healing within a range of 70% while only 0% reported no healing at all. Furthermore, the data showed no correlation between, age and weight of dogs being sampled. The healing effects of TPA seem to be present regardless of dog weight or age.

| Test Subject No. | Weight (US Pounds) | Age (months) | Wound Reduction Reported | Wound Reduction Within +-5% Completion |
|---|---|---|---|---|
| 1 | 60 | 36 | Yes | 90% |
| 2 | 13.22 | 132 | Yes | 70% |
| 3 | 65 | 36 | Yes | 100% |
| 4 | 60 | 7 | Yes | 90% |
| 5 | 62 | 36 | Yes | 90% |
| 6 | 13 | 8 | Yes | 100% |
| 7 | 45 | 48 | Yes | 90% |
| 8 | 15 | 7 | Yes | 90% |
| 9 | 20 | 60 | Yes | 90% |
| 10 | 15 | 12 | Yes | 90% |
| 11 | 10 | 144 | Yes | 100% |

More information regarding this study can be found in the appendix of this patent application. This application filing contains an appendix providing for a more detailed explanation of the results. This appendix is entitled Appendix to the Specification K9 Skin Rescue Evidence and is hereby incorporated by reference. The evidence from this study show the remarkable effects of the present disclosure and are not a very unexpected result of mixing sulfur, with a hydrocarbon, *Aloe vera* and few (5% or less) impurities. Treating an animal with TPA is not as simple as slathering the TPA on an animal like other ineffective creams and gels. A method of applying a therapeutically effective amount of a topical treatment (TPA) for an animal wound on an animal in need thereof comprises various steps. An animal must be properly selected from an area it inhabits. This is more complicated than selecting a human subject because often times animals are herded or socialized together. This is important because diseases such as mange, and skin irritation may spread through a herd if a herd is kept together or may be spread faster in an indoor kennel for dogs compared to an outdoor one. The best form of selecting an individual animal from a group or herd is to verify that the individual animal has skin irritation or other conditions such as cuts. Dogs or animals that interact with the particular subject animal should also be examined to verify they either have or do not have a skin irritation or other condition.

Next, the subject or subjects selected should have their medical history reviewed. Diseases affecting blood pressure (but not including heart worms) should exclude an animal from treatment. However, in some instances an animal that does have a heart condition or blood pressure conditions may be allowed to use TPA, an veterinarian or other healthcare provider should be consulted before using TPA. Muscle spasms or neurological disorders may also be a disqualifying event for the use of TPA on an animal, but an animal's veterinarian or other healthcare provider should be consulted before using TPA.

Next the wound on the particular animal subject should be measured to determine the correct amount of TPA to be applied to the wound. Wound measurements may be taken various ways. In some instances, a technician or healthcare provider or individual applying TPA may want to eyeball the wound and apply TPA based on simply looking at the wound. This method is not advised, especially for individuals applying TPA for the first time. Individuals with much experience measuring wounds and applying TPA may use this method because they have a sense of how much TPA should be applied. Inexperienced individuals may apply too much TPA. Applying too much TPA is not desired because TPA contains sulfur in it which in high enough amounts may actually irritate skin. Additionally, applying too much TPA may be uncomfortable to the animal. The animal may try and lick or get rid of the TPA.

One method of measuring a wound includes measuring the radius of the wound and determining the circumference of the wound. This may be accomplished via the formula $C=2\pi R$. In the event a wound is not a perfect circle, the wound should be treated as though it is a circle and the longest radius measured and the formula for circumference of a circle used. The centimeters of the wound should then be converted to milliliters (ml) of TPA and the appropriate amount of TPA used. For example, say a wound has a diameter of 4 cm, then the calculation would be (2)(4 cm wound radius)(3.14)=25.12 ml of TPA applied to the wound. From here the appropriate amount of TPA should be measured out before being applied to the wound.

Once the appropriate amount of TPA has been measured out, the wound site of the animal should be cleaned if muddy. Cleaning may consist of removing hairs, washing with warm water. Note the wound should be cleaned but not to such a degree where the animal's own oils are removed from the wound site. In the event the animal's own oils are removed from the site, the TPA may become less effective. A therapeutically effective amount of the animal's own oils should be left at the site. TPA may come in many forms. One possible form is a topical treatment for the treatment of animal wounds comprising 30%-33% by weight sulfur 30%-33% by weight *Aloe vera* or *Aloe vera* derivative 30-33% hydrocarbon polymer and at most 1% impurities. A more specific version would be 33 grams of sulfur, mixed with 33 grams of *Aloe vera* dust and 33 grams of petroleum jelly. A more specific version would be 33 grams of sulfur, mixed with 33 grams of *Aloe vera* gel and 33 grams of petroleum jelly. A more specific version would be 33 grams of sulfur, mixed with 16 grams of *Aloe vera* dust and 16 grams of *Aloe vera* gel and 33 grams of petroleum jelly.

Exact weight measurements may not be preferred because TPA when made industrially may be made in large batches. A range of appropriate weights may therefore be more important. A more specific version would be at least 33 grams of sulfur, mixed with at least 33 grams of *Aloe vera* gel and at least 33 grams of petroleum jelly. A more specific version would be at least 33 grams of sulfur, mixed with at least 16 grams of *Aloe vera* dust and at least 16 grams of *Aloe vera* gel and at least 33 grams of petroleum jelly. A more specific version would be between 30-35 grams of sulfur, mixed with at least 15-35 grams of *Aloe vera* dust and at least 15-35 grams of *Aloe vera* gel and at least 30-35 grams of petroleum jelly.

Other formulations may contain higher proportions of *Aloe vera* derivatives such as Veracylglucan and Acemannan. TPA production may follow a formula of at least 33 grams of sulfur, mixed with at least 33 grams of *Aloe vera* gel, that contains at least 10 mg of Veracylglucan and at least 33 grams of hydrogenated castor oil. Another formula may be Veracylglucan at least 33 grams of sulfur, mixed with at least 33 grams of *Aloe vera* gel, that contains at least 10 mg of Acemannan and at least 33 grams of hydrogenated castor oil.

Another The topical treatment of claim 1 wherein the *Aloe vera* derivative may be selected from a group consisting of *Aloe vera* extract, Veracylglucan ($C_{56}H_{82}O_{51}$), Acemannan $C_{66}H_{10}1NO_{49}$; wherein the hydrocarbon polymer may be selected from the group consisting of petroleum jelly hydrogenated castor oil and beeswax.

It should be noted that when *Aloe vera* or *Aloe vera* derivative is used to make TPA, as in the preceding paragraphs, the *Aloe vera* or *Aloe vera* derivative may be obtained via the species within the *Aloe* family, such as *Aloe vera, Aloe viridiflora, Aloe excelsa, Aloe thraskii*, and *Aloe namibensis*. Additionally, impurities may be found in the species of *Aloe vera* listed above. The impurities may include enzymes such as the enzyme amylase. Impurities that are tolerable for TPA, and may actually be preferred include those outlined in SEQUENCE ID 1, SEQUENCE ID 2, SEQUENCE ID 3, SEQUENCE ID 4, SEQUENCE ID 5, or SEQUENCE ID 6. Sometimes, if sequences are used as impurities the impurities must be selected from the group of sequence IDs consisting of SEQUENCE ID 1, SEQUENCE ID 2, SEQUENCE ID 3, SEQUENCE ID 4, SEQUENCE ID 5, or SEQUENCE ID 6. In other instances, if sequences are used as impurities the impurities must be selected from the group consisting essentially of SEQUENCE ID 1, SEQUENCE ID 2, SEQUENCE ID 3, SEQUENCE ID 4, SEQUENCE ID 5, or SEQUENCE ID 6.

Another method of making TPA involves selecting a specimen of *Aloe vera* from an *Aloe* plant. de-dusting the *Aloe vera* specimen; washing the *Aloe vera* specimen in warm water, the warm water being exposed to the *Aloe vera* plant for at least five seconds; removing the rind from the *Aloe vera* specimen; washing the specimen a second time in warm water, the warm water being exposed to the *Aloe vera* plant for at least five seconds; inserting the specimen into a dehydrating machine for at least twelve hours; examining the *Aloe vera* specimen and verifying that the specimen is no more than 5% liquid by weight and modifying the specimen if there is more than 5% liquid by dry weight; grinding up the *Aloe vera* specimen until it is a fine powder of *Aloe vera* granules; mixing the *Aloe vera* granules with wet *Aloe vera* extract to create a dry-wet *Aloe vera* complex; mixing the dry-wet *Aloe vera* complex with sulfur until the mixture becomes a homogeneous mixture of sulfur and granules; combining the homogeneous mixture with petroleum jelly and homogenizing the homogeneous mixture with the petroleum jelly until the entire mixture becomes homogenous TPA with no more than 1% impurities. It is crucial the *Aloe vera* be mixed with the sulfur before the petroleum jelly, because if either the sulfur or *Aloe vera* is mixed with petroleum jelly first, the sulfur or petroleum jelly may begin to prematurely rehydrate and render the TPA less effective. One embodiment of TPA includes A topical treatment for the treatment of animal wounds comprising: 30%-33% by weight sulfur; 30%-33% by weight *Aloe vera* or *Aloe vera* derivative; 30-33% by weight hydrocarbon polymer; at most 5% by weight impurities.

De-dusting the plant is very important. Some technicians have made the mistake of washing the specimen without de-dusting. This is a problem because large granules of debris that may be present on the plant can actually scratch and scar the *Aloe vera* leaves. This may make the *Aloe vera* or *Aloe vera* derivative obtained from the plant much less desirable. If one were to wash without de-dusting the specimen may be damaged. Additionally the granule size of the *Aloe vera* powder are very important. In TPA granules should have a diameter of 30-40 μm.

It is claimed:

1. A method of applying a therapeutically effective amount of a topical treatment for an animal wound on an animal in need thereof comprising:

selecting an individual animal from a group or herd of animals;

consulting the animal's medical history and verifying that the animal does not have a disease affecting blood pressure, muscles, or neural cells;

cleaning the wound and shaving off hair feathers, scales, fur, hair exoskeleton or other integument, but not disturbing the animal's natural oils or secretions;

applying an effective amount of a topical animal cream to the wound site;

wherein the topical animal cream comprises

30%-33% sulfur;

30%-33% *Aloe vera* or *Aloe vera* derivative, the *Aloe vera* or *Aloe vera* derivative comprising *Aloe vera* extract, Veracylglucan ($C_{56}H_{82}O_{51}$), and Acemannan $C_{66}H_{101}NO_{49}$ obtained from *Aloe vera, Aloe viridiflora, Aloe excelsa, Aloe thraskii*, and *Aloe namibensis;*

30-33% hydrocarbon polymer; and at most 5% impurities; and reapplying the topical animal cream every day for at least two weeks and until the wound has significantly decreased.

* * * * *

SEQUENCE LISTING

```
<160> NUMBER OF SEQ ID NOS: 6

<210> SEQ ID NO 1
<211> LENGTH: 731
<212> TYPE: PRT
<213> ORGANISM: Aloe vera

<400> SEQUENCE: 1

Met Pro Val Asp His Gly Ala His Asp Ala Leu Asp Asp Leu Leu Ala
1               5                   10                  15

Gly Arg His Pro Asp Pro Phe His Ile Leu Gly Pro His Ala Asp Gly
            20                  25                  30

Pro Arg Ser Trp Val Arg Val Leu Val Pro Asn Ala Glu Gln Val Thr
        35                  40                  45

Val Leu Leu Gly Ala Lys Asp Glu Glu Trp Pro Leu Thr His Val Arg
    50                  55                  60

His Gly Met Tyr Ser Gly Leu Val Asp Gly Leu Ala Pro Gly Gln Pro
65                  70                  75                  80

Thr Ala Tyr Arg Leu Arg Ile Lys Trp Pro Thr Gly Glu Gln Ile Thr
                85                  90                  95

Glu Asp Pro Tyr Ala Phe Ser Ala Leu Leu Gly Asp Leu Asp Leu His
            100                 105                 110

Leu Ile Ser Glu Gly Arg His Glu Tyr Leu Ala Asp Cys Leu Gly Ser
        115                 120                 125

His Val Met Asp Val Glu Gly Val Arg Gly Val Arg Phe Ala Val Trp
    130                 135                 140
```

-continued

```
Ala Pro Asn Ala Arg Arg Val Ser Val Val Gly Asp Phe Asn Ser Trp
145                 150                 155                 160

Asp Gly Arg Arg His Pro Met Arg Leu Arg His Ser Ala Gly Val Trp
                165                 170                 175

Glu Ile Phe Ile Pro Arg Leu Gln Ala Gly Thr Arg Tyr Lys Tyr Glu
            180                 185                 190

Ile Ala Gly Pro Glu Gly Gln Leu Leu Pro Leu Lys Ala Asp Pro Leu
        195                 200                 205

Ala Arg Gln Thr Glu Ala Pro Pro Ala Thr Ala Ser Ile Val Pro Asp
    210                 215                 220

Pro Thr Pro Tyr Thr Trp Thr Asp Asp Asp Trp Met Ala Thr Arg Ala
225                 230                 235                 240

Ala Arg Gln Ala Gln Asp Ala Pro Ile Thr Val Tyr Glu Val His Ala
                245                 250                 255

Gly Ser Trp Leu Pro Arg Asp Gly Glu Asp Asp Gly Glu Cys Val Trp
            260                 265                 270

Arg Arg Leu Ala Thr Arg Leu Val Pro Tyr Ala Arg Asp Leu Gly Phe
        275                 280                 285

Thr His Leu Glu Leu Met Pro Ile Met Glu His Pro Phe Gly Gly Ser
    290                 295                 300

Trp Gly Tyr Gln Pro Leu Gly Val Phe Ala Pro Thr Ala Arg Tyr Gly
305                 310                 315                 320

Thr Pro Arg Asp Phe Ala Ala Phe Val Asp Ala Cys His Ala Ala Gly
                325                 330                 335

Leu Ala Val Ile Leu Asp Trp Val Pro Ala His Phe Pro Thr Asp Thr
            340                 345                 350

His Gly Leu Ser His Phe Asp Gly Thr Ala Leu Tyr Glu Tyr Gln Asp
        355                 360                 365

Pro Arg Glu Gly Phe His Pro Asp Trp Asn Thr Leu Ile Tyr Asn Leu
    370                 375                 380

Gly Arg Thr Glu Val His Asn Phe Met Val Ala Ser Ala Leu Glu Trp
385                 390                 395                 400

Val Arg Arg Tyr His Ile Asp Gly Leu Arg Val Asp Ala Val Ala Ser
                405                 410                 415

Met Leu Tyr Arg Asp Tyr Ser Arg Ala Ala Gly Glu Trp Ile Pro Asn
            420                 425                 430

Arg Tyr Gly Gly Arg Glu Asn Leu Glu Ala Val Asp Phe Leu Arg Asp
        435                 440                 445

Met Asn Ala Thr Val His Arg Leu Cys Pro Gly Ala Ile Thr Val Ala
    450                 455                 460

Glu Glu Ser Thr Ala Trp Pro Gly Val Ser Ala Arg Thr Glu Asp Gly
465                 470                 475                 480

Gly Leu Gly Phe Ser Tyr Lys Trp Asn Met Gly Trp Met His Asp Thr
                485                 490                 495

Leu Arg Tyr Met His Asn Asp Pro Val His Arg Arg Tyr His His Asn
            500                 505                 510

Asp Met Thr Phe Gly Met Val Tyr Ala Tyr Ser Glu Arg Phe Ile Leu
        515                 520                 525

Pro Leu Ser His Asp Glu Val Val His Gly Lys Gly Ser Leu Leu Asn
    530                 535                 540

Lys Met Pro Gly Asp Arg Trp Gln Arg His Ala Asn Leu Arg Ala Tyr
545                 550                 555                 560

Phe Gly Phe Met Trp Gly His Pro Gly Lys Lys Leu Leu Phe Met Gly
```

```
                565                 570                 575

Gly Glu Ile Ala Gln Glu Arg Glu Trp Asn His Asp Ala Ser Leu Asp
            580                 585                 590

Trp Gly Ala Leu Asp Asp Gly Leu His Arg Gly Val Gln Lys Leu Val
        595                 600                 605

Arg Asp Leu Asn His Val Tyr Ala Glu Leu Pro Ala Leu His Arg His
    610                 615                 620

Asp His Asp Ala Ser Gly Phe Glu Trp Leu Ile Gly Asp Asp Tyr Ala
625                 630                 635                 640

Asn Ser Val Tyr Ala Phe Val Arg Arg Asp Gly Asp Ala Leu Ala Leu
                645                 650                 655

Val Val Cys Asn Phe Thr Pro Val Pro Arg Asp Gly Tyr Arg Ile Gly
            660                 665                 670

Val Pro Arg Ala Gly Arg Trp Arg Glu Arg Ile Asn Thr Asp Ala Gly
        675                 680                 685

Asp Tyr Gly Gly Ser Gly Met Gly Asn Ser Gly Gly Arg His Thr Glu
    690                 695                 700

Ala Val Ala Ala His Gly Arg Glu Gln Ser Leu Val Leu Thr Leu Pro
705                 710                 715                 720

Pro Leu Ala Thr Leu Ile Phe Gln Phe Glu Gly
                725                 730


<210> SEQ ID NO 2
<211> LENGTH: 1117
<212> TYPE: PRT
<213> ORGANISM: Aloe vera

<400> SEQUENCE: 2

Met Arg Ile Tyr Tyr Val His Pro Leu His Val Gly Ser Leu Ser Gly
1               5                   10                  15

Asp Ser Phe Ser His Trp Gln Ala Arg Cys Ala Arg Ile Lys Ser Leu
            20                  25                  30

Gly Phe Asp Thr Leu Met Thr Ala Pro Leu Trp Ala Pro Asp Pro Ala
        35                  40                  45

Gly Asn Pro Tyr Val Pro Asp Asp Pro Asp Arg Leu His Pro Ala Leu
    50                  55                  60

Gly Asp Met Asp Leu Ala Ala Ala Met Thr Ala Leu Ser Arg Leu Cys
65                  70                  75                  80

Gly Glu His Gly Leu Ala Leu Met Ile Asp Leu Pro Leu Glu Lys Val
                85                  90                  95

Ala Ile Asp Gly Ala Ala Ala Arg Ala His Pro His Trp Tyr Glu Asp
            100                 105                 110

Ala Gly Gly Asp Ala Leu Leu Asp Pro Arg Arg Pro Trp Glu Asp Arg
        115                 120                 125

His Ala Leu Pro Leu Arg Arg Glu His Gly Arg Ala Pro Ala Gly Phe
    130                 135                 140

Val Asp His Trp Ile Glu Arg Leu Gly Leu Trp Val Glu Asn Gly Val
145                 150                 155                 160

Ala Gly Phe Arg Cys Glu Gly Leu Ala Gln Leu Ala Pro Ala Asp Trp
                165                 170                 175

Arg Asp Leu Ile Gln Gly Val Arg Ala Val Arg Pro Asp Cys Arg Trp
            180                 185                 190

Leu Ala Trp Thr Pro Gly Val Ala Pro Trp Asp Val Ala Pro Leu Ala
        195                 200                 205
```

-continued

```
Gly Val Gly Phe Asp Gly Val Phe Ser Ser Phe Pro Trp Trp Asp Tyr
    210                 215                 220

Arg Ala Glu Trp Leu Leu Glu Glu Thr Asp Arg Leu Arg Ala Ile Ala
225                 230                 235                 240

Pro Val Ile Ala Pro Val Glu Ala Pro Tyr Ala Lys Arg Val Ala Ser
                245                 250                 255

Trp Arg Ser Asp Pro Ala Gly Arg Tyr Arg Asn Ala Ala Arg Ala Val
            260                 265                 270

Trp Thr Ala Ala Val Val Gly Asp Gly Val Leu Val Pro Met Gly Phe
        275                 280                 285

Glu Asp Ala Ala Thr His Ala Leu Glu Arg Asp Gly Ser Gly Val Arg
    290                 295                 300

Glu Asp Pro Gln Gly Asp Pro Gly Leu His Ile Asp Ile Gly Arg Ala
305                 310                 315                 320

Asn Gln Trp Leu Ala Arg Thr Ala Ser Ala Arg Gly Pro Leu His Ser
                325                 330                 335

Leu Gln Gly Pro His Thr Gly Val Thr Ala Leu Phe Arg Gly Asp Gly
            340                 345                 350

Ala Ala Thr Pro Ala Ala Gly Ala Gly Arg Gly Ser Ala Arg Leu Ile
        355                 360                 365

Val Leu Asn Pro Ser Asp Asp Val Ala Ala Ser Pro Asp Trp Asp Ala
    370                 375                 380

Leu Arg Ala Arg Leu Pro Asp Gly Tyr Gly Arg Leu Asp Gln Trp Asp
385                 390                 395                 400

Ala Asp Arg Pro Ala Gln Asp Leu Pro Thr Thr Leu Ala Pro Gly Asp
                405                 410                 415

Met Leu Arg Leu Gly Ala Ser Arg Leu Pro Pro Val Thr Val Pro Ala
            420                 425                 430

Ser Asp Asp Thr Arg Leu Gly Val Thr Ala Ala Met Arg Gln Pro Arg
        435                 440                 445

Leu Ala Ile Glu His Val Thr Pro Ala Val Asp Asp Gly Ala Phe Pro
    450                 455                 460

Ile Lys Arg Ile Ala Gly Glu Thr Ile Thr Val Glu Ala Asp Val Phe
465                 470                 475                 480

Cys Asp Gly His Glu Tyr Ile Ala Val Ala Leu Leu Trp Arg Ala Ala
                485                 490                 495

Asp Asp Lys Glu Trp Gln Arg Val Pro Met Thr Pro Leu Gly Asn Asp
            500                 505                 510

Arg Trp Thr Ala Ser Phe Ala Pro Ala Arg Ile Gly Arg His Tyr Tyr
        515                 520                 525

Ala Val Gln Gly Trp Asp Asp Ala Trp Thr Thr Phe Arg Asp Gly Leu
    530                 535                 540

Glu Lys Lys Tyr Arg Ala Gly Val Asp Ile Ala Leu Glu Thr Ala Glu
545                 550                 555                 560

Gly Arg Gly Leu Val Gln Glu Ala Leu Glu Arg Leu Pro Asp Thr Ala
                565                 570                 575

Glu Thr Ser Ala Ala Ala Leu Arg Gln Val Leu Arg Val Leu Gly Ala
            580                 585                 590

Ala Pro Ala Glu Lys Pro Arg Arg Asp Arg Lys Lys Ser Ala Gly Glu
        595                 600                 605

Ala Ser Pro Pro Arg Phe Pro Ser Pro Thr Pro Asp Gln Val Ala Ala
    610                 615                 620

Leu Leu Asp Ala Ala Thr Ala Arg Ala Met Arg Glu Ala Asp Asp Arg
```

-continued

```
625                 630                 635                 640

Arg Phe Glu Thr Thr Ser Ala Ile Tyr Pro Val Thr Val Asp Arg Pro
                645                 650                 655

Ala Ala Ile Phe Ser Ser Trp Tyr Glu Ile Phe Pro Arg Ser Gln Ser
            660                 665                 670

Gly Asp Pro Arg Arg His Gly Thr Phe Asp Asp Val Ile Ala Thr Leu
        675                 680                 685

Pro Arg Val Arg Ala Met Gly Phe Asp Thr Leu Tyr Phe Pro Pro Ile
    690                 695                 700

His Pro Ile Gly Ala Arg Asn Arg Lys Gly Arg Asn Asn Ser Leu Gln
705                 710                 715                 720

Ala Gly Pro Asp Asp Pro Gly Ser Pro Tyr Ala Ile Gly Ser Glu Asp
                725                 730                 735

Gly Gly His Asp Ala Leu His Pro Gln Leu Gly Thr Leu Asp Asp Phe
            740                 745                 750

Arg Arg Leu Val Ala Ala Ala Arg Ala His Gly Leu Glu Leu Ala Leu
        755                 760                 765

Asp Phe Ala Ile Gln Cys Ser Pro Asp His Pro Trp Leu Lys Ala His
    770                 775                 780

Pro Glu Trp Phe Asp Trp Arg Pro Asp Gly Ser Leu Lys Tyr Ala Glu
785                 790                 795                 800

Asn Pro Pro Lys Lys Tyr Glu Asp Ile Val Asn Val Asp Phe Tyr Gly
                805                 810                 815

Ala Lys Pro Gly Ala Ser Arg Gln Ala Pro Leu Trp Arg Ala Leu Arg
            820                 825                 830

Asp Val Val Leu Phe Trp Val Ala Gln Gly Val Arg Val Phe Arg Val
        835                 840                 845

Asp Asn Pro His Thr Lys Pro Leu Pro Phe Trp Glu Trp Met Ile Gly
    850                 855                 860

Asp Val Gln Gly Arg His Pro Asp Val Leu Phe Leu Ser Glu Ala Phe
865                 870                 875                 880

Thr Arg Pro Lys Met Met Tyr Arg Leu Ala Lys Val Gly Phe Ser Gln
                885                 890                 895

Ser Tyr Thr Tyr Phe Thr Trp Arg Glu Thr Lys Gln Glu Phe Thr Glu
            900                 905                 910

Tyr Leu Thr Glu Leu Thr Gln Gly Pro Pro Ala Asp Phe Phe Arg Pro
        915                 920                 925

His Phe Phe Val Asn Thr Pro Asp Ile Asn Pro Arg Phe Leu Gln Gln
    930                 935                 940

Ser Gly Arg Gly Gly Phe Leu Ile Arg Ala Ala Leu Ala Ala Thr Leu
945                 950                 955                 960

Ser Gly Leu Trp Gly Val Tyr Asn Gly Phe Glu Leu Cys Glu Ala Ser
                965                 970                 975

Ala Val Pro Gly Lys Glu Glu Tyr Leu Asp Ser Glu Lys Tyr Glu Ile
            980                 985                 990

Arg Ala Trp Asp His Glu Arg Pro  Gly Asn Ile Val Arg  Glu Ile Thr
        995                 1000                1005

Arg Leu  Asn Ala Ile Arg Arg  Ala Asn Pro Ala Leu  His Thr His
    1010                1015                1020

Leu Gly  Val Arg Trp His Thr  Ala Trp Asp Asp Gln  Val Leu Phe
    1025                1030                1035

Phe Ser  Lys Ser Thr Pro Gln  Arg Asp Asn Val Leu  Leu Val Ala
    1040                1045                1050
```

```
Ile Ser  Leu Asp Pro His His  Pro Arg Asp Val Val  Leu Glu Ile
    1055                 1060                 1065

Pro Met  Trp Glu Phe Gly Leu  Pro Asp Asp Gly Pro  Leu Gln Ala
    1070                 1075                 1080

Glu Asp  Leu Ile Asp Gly Asn  Arg Met Val Trp Arg  Gly Lys Gln
    1085                 1090                 1095

Gln Gly  Val His Leu His Pro  Asp Gln Pro Tyr Arg  Ile Trp Arg
    1100                 1105                 1110

Val Thr  Pro Ala
    1115


<210> SEQ ID NO 3
<211> LENGTH: 611
<212> TYPE: PRT
<213> ORGANISM: Aloe Vera

<400> SEQUENCE: 3

Met Thr Ala Ser Val Pro Ala Val Ser Tyr Ser His Gly Ala Val Arg
1               5                   10                  15

Gln Ala Gly Gly Arg Thr Arg Phe Arg Leu Trp Ala Pro Asn Ala Asn
            20                  25                  30

Asp Gly Val Val Leu Glu Ile Ala Gly His Glu Pro Leu Pro Met Arg
        35                  40                  45

Val Val Ala Asp Gly Tyr Tyr Glu Ile Asp Ala Asp Cys Glu Pro Gly
    50                  55                  60

Ala Arg Tyr Arg Tyr Arg Val Ala Pro Asp Leu Ala Val Pro Asp Pro
65                  70                  75                  80

Ala Ser Arg Leu Gln Ala Gly Asp Val His Asp Asp Ser Val Val Val
                85                  90                  95

Asp Gly Gly Asp Ala Tyr Ala Trp Arg His Pro Asp Trp Arg Gly Arg
            100                 105                 110

Pro Trp Thr Glu Thr Val Leu Tyr Glu Val His Pro Gly Leu Ala Gly
        115                 120                 125

Gly Tyr Ala Gly Ile Glu Gln Arg Leu Pro Glu Leu Ala Ala Leu Gly
    130                 135                 140

Ile Thr Ala Ile Glu Leu Met Pro Ile Ala Asp Phe Pro Gly Pro Arg
145                 150                 155                 160

Asn Trp Gly Tyr Asp Gly Val Leu Pro Tyr Ala Pro Asp Arg Ala Tyr
                165                 170                 175

Gly Asp Pro Asp Glu Leu Arg Arg Leu Ile Asp Thr Ala His Gly Leu
            180                 185                 190

Gly Met Met Val Phe Leu Asp Val Val Tyr Asn His Phe Gly Pro Asp
        195                 200                 205

Gly Asn Tyr Leu Asn Ala Tyr Ala Ala Asp Phe Phe Arg Gln Asp Leu
    210                 215                 220

Gln Thr Pro Trp Gly Ala Ala Ile Asp Phe Arg Arg Pro Gln Val Arg
225                 230                 235                 240

Arg Tyr Phe Ala Glu Asn Ala Leu Tyr Trp Leu Ala Glu Tyr Arg Phe
                245                 250                 255

Asp Gly Leu Arg Leu Asp Ala Val His Ala Ile Arg Asp Val Gly Trp
            260                 265                 270

Leu Glu Glu Met Ala Ala Phe Val Arg Ala His Ile Asp Pro Gly Arg
        275                 280                 285

His Val His Leu Val Leu Glu Asn Asp Asp Asn Gln Val His Pro Leu
```

```
    290                 295                 300

Leu His Gly Tyr Gln Ala Gln Trp Asn Asp Asp Ala His His Val Leu
305                 310                 315                 320

His His Leu Leu Thr Gly Glu Ser Glu Gly Tyr Tyr Glu Asp Tyr Val
                325                 330                 335

Glu Gln Pro Ala Gln Arg Leu Ala Arg Ala Leu Thr Glu Gly Phe Val
            340                 345                 350

Tyr Gln Gly Gln Pro Ser Arg His Arg Gly Gly Gln Arg Arg Gly Glu
        355                 360                 365

Arg Ser Asp Leu Leu Pro Pro Thr Ala Phe Val Phe Phe Leu Gln Asn
    370                 375                 380

His Asp Gln Thr Gly Asn Arg Ala Leu Gly Glu Arg Leu Gly Pro Leu
385                 390                 395                 400

Leu Arg Asp Ala Arg Ile Leu Lys Ala Ala Thr Ala Leu Gln Leu Leu
                405                 410                 415

Thr Pro Gln Ile Pro Leu Ile Phe Met Gly Glu Glu Arg Gly Ala Thr
            420                 425                 430

Thr Pro Phe Leu Tyr Phe Thr Ser His Ala Asp Pro Gln Leu Ala Thr
        435                 440                 445

Ala Val Arg Asp Gly Arg Arg Lys Glu Phe Gln His Phe Arg Ala Phe
    450                 455                 460

Ala Asn Pro Ala Met Arg Glu Arg Ile Pro Asp Pro Asn Asp Pro Ala
465                 470                 475                 480

Thr Tyr Ala Asn Ala Asn Pro Phe Thr Gly Glu Pro Asp Ala Asp Thr
                485                 490                 495

Leu Ala Thr Tyr Thr Glu Leu Leu Ala Val Arg Arg Arg Glu Ile Val
            500                 505                 510

Pro Arg Leu Gln Gly Ala His Ala Leu Gly Ala His Val Leu Gly Leu
        515                 520                 525

Arg Ala Val Val Ala Gln Trp Arg Met Gly Asp Gly Ala Thr Leu Thr
    530                 535                 540

Leu Tyr Ala Asn Leu Gly Gly Val Asp Leu Arg Pro Asp Trp Leu Gln
545                 550                 555                 560

Val Asp Leu Ala Asp Gln Ala Val Val Tyr Glu Ser Glu Thr Gly Ala
                565                 570                 575

Gly Ala Ala Leu His Glu Gly Leu Leu Trp Arg Gly Cys Thr Ile Ala
            580                 585                 590

Leu Leu Gln Ala Pro Val Ala Gly Ala Arg Met Thr Thr Asp Thr Lys
        595                 600                 605

Glu Tyr Pro
    610


<210> SEQ ID NO 4
<211> LENGTH: 1159
<212> TYPE: PRT
<213> ORGANISM: Aloe Vera

<400> SEQUENCE: 4

Met Ala Arg Gln Ala Thr Gly Arg Ala Pro Ala Pro Arg Pro Ala Val
1               5                   10                  15

Pro His Leu Ala Ser Asp Ala Arg Leu Asn Ala Gln Pro Gly Arg Val
            20                  25                  30

Pro Arg Pro Ala Gln Arg Gln Glu Asp Asn Gly Met Ser Asp Asn His
        35                  40                  45
```

-continued

```
Val Asn Ser Pro Asn Arg Asp Asp Pro Leu Trp Tyr Lys Asp Ala Val
    50                  55                  60

Ile Tyr Gln Leu His Val Lys Ser Phe Phe Asp Ala Asn Asn Asp Gly
65                  70                  75                  80

Val Gly Asp Phe Ala Gly Leu Val Glu Lys Leu Asp Tyr Ile Ala Ser
                85                  90                  95

Leu Gly Val Asn Thr Ile Trp Leu Leu Pro Phe Tyr Pro Ser Pro Arg
            100                 105                 110

Arg Asp Asp Gly Tyr Asp Ile Ala Glu Tyr Arg Gly Val His Pro Asp
        115                 120                 125

Tyr Gly Thr Leu Ala Gly Val Arg Lys Leu Ile Lys Ala Ala His Ala
    130                 135                 140

Arg Gly Leu Arg Val Ile Thr Glu Leu Val Val Asn His Thr Ser Asp
145                 150                 155                 160

Gln His Pro Trp Phe Gln Arg Ala Arg Arg Ala Lys Pro Gly Ser Ala
                165                 170                 175

Ala Arg Asn Tyr Tyr Val Trp Ser Asp Asn Asp Gln Ala Tyr Ala Gly
            180                 185                 190

Thr Arg Ile Ile Phe Leu Asp Thr Glu Lys Ser Asn Trp Thr Trp Asp
        195                 200                 205

Pro Val Ala Gly Ala Tyr Phe Trp His Arg Phe Tyr Ser His Gln Pro
    210                 215                 220

Asp Leu Asn Tyr Asp Asn Pro Gln Val Leu Lys Glu Val Ile Gly Val
225                 230                 235                 240

Met Arg Phe Trp Leu Asp Leu Gly Val Asp Gly Leu Arg Leu Asp Ala
                245                 250                 255

Val Pro Tyr Leu Val Glu Arg Glu Gly Thr Asn Asn Glu Asn Leu Pro
            260                 265                 270

Glu Thr His Ala Val Leu Lys Lys Ile Arg Ala Gln Leu Asp Ala Glu
        275                 280                 285

Tyr Pro Gly Arg Met Leu Leu Ala Glu Ala Asn Gln Trp Pro Glu Asp
    290                 295                 300

Ala Gln Glu Tyr Phe Gly Gln Gly Asp Glu Cys His Met Ser Phe His
305                 310                 315                 320

Phe Pro Leu Met Pro Arg Met Tyr Met Ala Ile Ala Arg Glu Asp Arg
                325                 330                 335

Phe Pro Ile Thr Asp Ile Met Arg Gln Thr Pro Asp Ile Pro Glu Thr
            340                 345                 350

Cys Gln Trp Ala Ile Phe Leu Arg Asn His Asp Glu Leu Thr Leu Glu
        355                 360                 365

Met Val Thr Ser Asn Glu Arg Asp Tyr Leu Trp Asn Thr Tyr Ala Ala
    370                 375                 380

Asp Arg Arg Ala Arg Ile Asn Leu Gly Ile Arg Arg Arg Leu Ala Pro
385                 390                 395                 400

Leu Met Glu Arg Asp Arg Arg Arg Ile Glu Leu Met Asn Ser Leu Leu
                405                 410                 415

Leu Ser Met Pro Gly Thr Pro Val Ile Tyr Tyr Gly Asp Glu Leu Gly
            420                 425                 430

Met Gly Asp Asn Ile His Leu Gly Asp Arg Asp Gly Val Arg Thr Pro
        435                 440                 445

Met Gln Trp Ser Pro Asp Arg Asn Gly Gly Phe Ser Arg Ala Asp Pro
    450                 455                 460

Glu Arg Leu Pro Leu Pro Pro Leu Met Gly Pro Leu Tyr Gly Tyr Glu
```

-continued

```
465                 470                 475                 480

Ala Val Asn Val Glu Ala Gln Gln Arg Asp Pro His Ser Leu Leu Asn
                485                 490                 495

Trp Ser Arg Arg Met Leu Ala Thr Arg Ala Lys Thr Gln Ala Phe Gly
            500                 505                 510

Arg Gly Thr Leu Arg Phe Leu Phe Pro Gly Asn Arg Asn Ile Leu Ala
        515                 520                 525

Tyr Leu Arg Glu Tyr Glu Ala Thr Thr Ile Leu Cys Val Ala Asn Leu
    530                 535                 540

Ser Arg Ala Ser Gln Pro Val Glu Leu Asp Leu Ser Ser Leu Ala Gly
545                 550                 555                 560

Arg Val Pro Val Glu Leu Leu Gly Gly Thr Pro Phe Pro Ala Ile Gly
                565                 570                 575

Glu Leu Thr Tyr Leu Leu Thr Leu Pro Pro Tyr Gly Phe Tyr Trp Phe
            580                 585                 590

Asp Leu Ser Ala Ser Ala Ser Pro Pro Glu Trp His Ala Thr His Pro
        595                 600                 605

Glu Arg Met Pro Glu Tyr Tyr Thr Leu Val Leu Arg Gly Arg Thr Gly
    610                 615                 620

Tyr Glu Leu Thr Glu Gly Ala Val Arg Ser Leu Arg Glu Asp Val Leu
625                 630                 635                 640

Pro Leu Tyr Leu Ser Arg Gln Arg Trp Tyr Pro Lys Asp Arg Lys Val
                645                 650                 655

Lys Met Ala Gln Ala Ala Tyr Ala Ala Gln Leu Pro Gly Ala Asp His
            660                 665                 670

Glu Cys Phe Ile Ala Glu Ile Gln Val Asp Phe Asp Gly Lys Pro Ala
        675                 680                 685

Arg Phe Leu Leu Pro Ala Ala Leu Ile Trp Asp Glu Thr Leu Pro Pro
    690                 695                 700

Met Ala Gln Gln Tyr Ala Leu Ala Arg Val Arg Arg Ala Ala Glu Met
705                 710                 715                 720

Gly Tyr Leu Thr Asp Ala Phe Thr Leu Pro Ser Phe Ile His Ala Leu
                725                 730                 735

Val Arg Gly Leu Arg Glu Arg Thr Glu Ile Pro Val Pro Arg Ala His
            740                 745                 750

Pro Pro Ala Val Leu Arg Phe Arg Gly Glu Pro Thr Leu Asp Lys Ile
        755                 760                 765

Glu Leu Pro Pro Asp Ala Glu Val Gln Trp Phe Thr Gly Glu Gln Ser
    770                 775                 780

Asn Ser Ser Val Thr Leu Gly Gly Ile Met Met Leu Lys Leu Leu Arg
785                 790                 795                 800

Arg Ile Val Pro Gly Val His Pro Glu Ala Glu Met Thr Arg Arg Leu
                805                 810                 815

Thr Glu Val Gly Tyr Ala Asn Gly Ala Pro Leu Leu Gly Glu Ile Gln
            820                 825                 830

Arg Ile Asp Glu Asp Gly Thr Pro His Thr Leu Ala Leu Met His Gln
        835                 840                 845

Met Ile Thr Asn Gln Gly Asp Ala Trp Thr Trp Thr Leu Asn Tyr Leu
    850                 855                 860

Lys Arg Thr Leu Glu Ala Ala Ala Leu Thr Ala Glu Ser Ala Glu Asp
865                 870                 875                 880

Tyr Asp Glu Asp Leu Leu Gly Tyr Ile Asn Phe Ala His Thr Met Gly
                885                 890                 895
```

-continued

Lys Arg Leu Gly Glu Leu His Ala Ala Leu Ser Leu Pro Thr Asp Asp
900 905 910

Ala Ala Phe Lys Pro His Arg Ala Thr Arg His Asp Ala Glu Arg Arg
915 920 925

Ala Lys Ala Val Ile Ala Met Leu Asp Gln Gly Leu Asp Thr Leu Lys
930 935 940

Ala Asn Met Gly Arg Leu Asp Ala Ala His Ala Glu Thr Ala Ala Trp
945 950 955 960

Leu Ala Glu His Arg Asp Ala Leu Val Glu Val Val Arg Asp Leu Ala
965 970 975

Ala Asn Glu Glu Asp Thr Leu His Ile Arg Ile His Gly Asp Phe His
980 985 990

Leu Gly Gln Val Leu Ala Ala Gln Gly Asp Ala Tyr Leu Ile Asp Phe
995 1000 1005

Glu Gly Glu Pro Ala Arg Thr Leu Glu Glu Arg Arg Ala Lys Thr
1010 1015 1020

Ser Ala Leu Arg Asp Val Ala Gly Leu Leu Arg Ser Phe Asp Tyr
1025 1030 1035

Ala Ala Ala Thr Leu Ala Asp Gly Thr Gly Lys Gly Lys Gly Lys
1040 1045 1050

Ala Glu Glu Thr Gly Glu Ala Gln Ile Ala Glu Gln Gln Leu Arg
1055 1060 1065

Thr Arg Arg Gln Asp Leu Ile Glu Arg Phe Arg Val Thr Ala Gly
1070 1075 1080

Glu Ser Phe Leu Ala Gly Tyr Arg Glu Val Ala His Thr Thr Glu
1085 1090 1095

His Pro Trp Ile Thr Pro Glu Val Glu Ala Pro Leu Ile Asp Leu
1100 1105 1110

Ala Leu Ile Glu Lys Ala Ala Tyr Glu Val Arg Tyr Glu Ala Ala
1115 1120 1125

His Arg Pro Asp Trp Val Gly Ile Pro Leu Ala Gly Leu Ala Ser
1130 1135 1140

Leu Ala Ala Arg Leu Leu Ser Asp Gly Ser Ala Ala Ser Ser His
1145 1150 1155

Pro

<210> SEQ ID NO 5
<211> LENGTH: 748
<212> TYPE: PRT
<213> ORGANISM: Aloe Vera

<400> SEQUENCE: 5

Met Pro Asn Gln Pro Arg Ile Thr Glu Gly Ser Pro Phe Pro Leu Gly
1 5 10 15

Ala Thr Leu Asp Asp Asp Gly Val Asn Phe Ala Leu Phe Ser Ala His
20 25 30

Ala Thr Lys Val Glu Leu Cys Leu Phe Asp Glu Leu Gly Glu Gln Glu
35 40 45

Thr Glu Arg Ile Val Leu Pro Glu Phe Thr Asp Glu Ile Trp His Val
50 55 60

His Val Ala Gly Leu Asn Ala Gly Thr Val Tyr Gly Tyr Arg Val His
65 70 75 80

Gly Pro Tyr Glu Pro Glu Asn Gly His Arg Phe Asn Pro Asn Lys Leu
85 90 95

-continued

```
Leu Leu Asp Pro Tyr Ala Lys Ala Tyr Val Gly Glu Leu Lys Trp Asp
            100                 105                 110

Pro Ala Val Phe Gly Tyr Pro Ile Gly Asp Glu Gln Ala Asp Leu Gly
        115                 120                 125

Phe Asp Glu Arg Asp Ser Ala Ala Phe Val Pro Lys Cys Arg Val Val
    130                 135                 140

Asp Gln Arg Phe Thr Trp Thr His Ala Thr Arg Val Arg Val Pro Trp
145                 150                 155                 160

Glu Arg Thr Ile Phe Tyr Glu Thr His Val Arg Gly Tyr Thr Met Arg
                165                 170                 175

His Pro Ala Val Pro Glu Ala Leu Arg Gly Ser Phe Ala Gly Leu Ala
            180                 185                 190

Arg Asp Ala Val Ile Asp His Ile Lys Ser Leu Gly Val Thr Ser Val
        195                 200                 205

Glu Leu Leu Pro Ile His Ala Phe Val Asn Asp Ser His Leu Leu Glu
    210                 215                 220

Gln Gly Leu Thr Asn Tyr Trp Gly Tyr Asn Thr Ile Gly Phe Phe Ala
225                 230                 235                 240

Pro Asp Pro Arg Tyr Phe Ser Gln Val Pro Gly Ala Ile Thr Glu Leu
                245                 250                 255

Lys Gln Met Ile Asp Arg Phe His Glu Ala Gly Leu Glu Ile Ile Leu
            260                 265                 270

Asp Val Val Tyr Asn His Thr Ala Glu Gly Ser Glu Leu Gly Pro Thr
        275                 280                 285

Leu Ser Phe Arg Gly Ile Asp Asn Ala Ser Tyr Tyr Arg Leu Leu Pro
    290                 295                 300

Asp Gln Lys Arg Tyr Tyr Ile Asn Asp Thr Gly Thr Gly Asn Thr Leu
305                 310                 315                 320

Asn Leu Ser His Pro Arg Val Leu Gln Met Val Met Asp Ser Leu Arg
                325                 330                 335

Tyr Trp Val Thr Glu Met Lys Val Asp Gly Phe Arg Phe Asp Leu Ala
            340                 345                 350

Thr Ile Leu Ala Arg Glu Pro Asp Gly Phe Asp Tyr Asn Ser Gly Phe
        355                 360                 365

Leu Lys Ala Cys Arg Gln Asp Pro Ile Leu Ser Ser Val Lys Leu Ile
    370                 375                 380

Ala Glu Pro Trp Asp Cys Gly Pro Gly Gly Tyr Gln Val Gly Asn Phe
385                 390                 395                 400

Pro Pro Gly Trp Ala Glu Trp Asn Asp Arg Tyr Arg Asp Thr Val Arg
                405                 410                 415

Ala Phe Trp Lys Gly Asp Glu Gly Met Ala Pro Glu Leu Ala Gly Arg
            420                 425                 430

Ile Thr Gly Ser Gly Gly Asp Phe Asn His Gly Gly Arg Arg Pro Trp
        435                 440                 445

Ala Ser Val Asn Phe Leu Thr Ala His Asp Gly Tyr Thr Leu Asn Asp
    450                 455                 460

Leu Val Ser Tyr Asn Asp Lys His Asn Glu Ala Asn Gly Glu Asp Asn
465                 470                 475                 480

Arg Asp Gly His Ser Asp Asn Arg Ser Trp Asn Cys Gly Ala Glu Gly
                485                 490                 495

Pro Thr Asp Asp Pro Asp Ile Arg Ala Leu Arg Glu Arg Gln Lys Arg
            500                 505                 510
```

Asn Met Leu Ala Thr Leu Leu Phe Ser Gln Gly Thr Pro Met Ile Val
515 520 525

Ala Gly Asp Glu Phe Gly Arg Thr Gln Gln Gly Asn Asn Asn Ala Tyr
530 535 540

Cys Gln Asp Asn Glu Ile Ser Trp Val Asp Trp Glu Ile Asn Glu Asp
545 550 555 560

Gly Ala Ala Leu Ile Glu Phe Leu Arg Lys Leu Thr Thr Leu Arg His
565 570 575

Thr Leu Pro Val Leu Arg Arg Gly Arg Phe Leu Thr Gly Asp Tyr Asp
580 585 590

Glu Ser Met Asp Val Ala Asp Val Lys Trp Leu Ser Ser Ser Gly Glu
595 600 605

Ala Leu Thr Pro Glu Gln Trp Ala Asp Thr Asn Met Arg Cys Phe Gly
610 615 620

Leu Ile Ile Asp Gly Arg Ala Arg Ala Thr Gly Ile Arg Arg Pro Ala
625 630 635 640

Ser Asp Ala Thr Leu Leu Leu Ile Phe Asn Ala Tyr His Asp Val Val
645 650 655

Asp Phe Thr Leu Pro Glu Ile Pro Gly Asn Asp Arg Trp Thr Cys Leu
660 665 670

Ile Asp Thr Asn Ala Pro Val Arg Ala Glu Leu Pro Gln Phe Ala Ser
675 680 685

Gly Asp Val Tyr Gln Val Thr Gly Arg Ser Leu Leu Leu Phe Ser Leu
690 695 700

Gln Ala Lys Gly Pro Thr Gln Arg Val Phe Asp Lys Leu Glu Glu Ala
705 710 715 720

Leu Thr Asp Glu Glu Thr Pro Glu Pro Ala Arg Glu Ala Ala Ala Ile
725 730 735

Val Lys Lys Ser Val Lys Lys Glu Lys Pro Ser Lys
740 745

<210> SEQ ID NO 6
<211> LENGTH: 748
<212> TYPE: PRT
<213> ORGANISM: Aloe vera

<400> SEQUENCE: 6

Met Pro Asn Gln Pro Arg Ile Thr Glu Gly Ser Pro Phe Pro Leu Gly
1 5 10 15

Ala Thr Leu Asp Asp Asp Gly Val Asn Phe Ala Leu Phe Ser Ala His
20 25 30

Ala Thr Lys Val Glu Leu Cys Leu Phe Asp Glu Leu Gly Glu Gln Glu
35 40 45

Thr Glu Arg Ile Val Leu Pro Glu Phe Thr Asp Glu Ile Trp His Val
50 55 60

His Val Ala Gly Leu Asn Ala Gly Thr Val Tyr Gly Tyr Arg Val His
65 70 75 80

Gly Pro Tyr Glu Pro Glu Asn Gly His Arg Phe Asn Pro Asn Lys Leu
85 90 95

Leu Leu Asp Pro Tyr Ala Lys Ala Tyr Val Gly Glu Leu Lys Trp Asp
100 105 110

Pro Ala Val Phe Gly Tyr Pro Ile Gly Asp Glu Gln Ala Asp Leu Gly
115 120 125

Phe Asp Glu Arg Asp Ser Ala Ala Phe Val Pro Lys Cys Arg Val Val
130 135 140

-continued

```
Asp Gln Arg Phe Thr Trp Thr His Ala Thr Arg Val Arg Val Pro Trp
145                 150                 155                 160

Glu Arg Thr Ile Phe Tyr Glu Thr His Val Arg Gly Tyr Thr Met Arg
                165                 170                 175

His Pro Ala Val Pro Glu Ala Leu Arg Gly Ser Phe Ala Gly Leu Ala
            180                 185                 190

Arg Asp Ala Val Ile Asp His Ile Lys Ser Leu Gly Val Thr Ser Val
        195                 200                 205

Glu Leu Leu Pro Ile His Ala Phe Val Asn Asp Ser His Leu Leu Glu
    210                 215                 220

Gln Gly Leu Thr Asn Tyr Trp Gly Tyr Asn Thr Ile Gly Phe Phe Ala
225                 230                 235                 240

Pro Asp Pro Arg Tyr Phe Ser Gln Val Pro Gly Ala Ile Thr Glu Leu
                245                 250                 255

Lys Gln Met Ile Asp Arg Phe His Glu Ala Gly Leu Glu Ile Ile Leu
            260                 265                 270

Asp Val Val Tyr Asn His Thr Ala Glu Gly Ser Glu Leu Gly Pro Thr
        275                 280                 285

Leu Ser Phe Arg Gly Ile Asp Asn Ala Ser Tyr Tyr Arg Leu Leu Pro
    290                 295                 300

Asp Gln Lys Arg Tyr Tyr Ile Asn Asp Thr Gly Thr Gly Asn Thr Leu
305                 310                 315                 320

Asn Leu Ser His Pro Arg Val Leu Gln Met Val Met Asp Ser Leu Arg
                325                 330                 335

Tyr Trp Val Thr Glu Met Lys Val Asp Gly Phe Arg Phe Asp Leu Ala
            340                 345                 350

Thr Ile Leu Ala Arg Glu Pro Asp Gly Phe Asp Tyr Asn Ser Gly Phe
        355                 360                 365

Leu Lys Ala Cys Arg Gln Asp Pro Ile Leu Ser Ser Val Lys Leu Ile
    370                 375                 380

Ala Glu Pro Trp Asp Cys Gly Pro Gly Gly Tyr Gln Val Gly Asn Phe
385                 390                 395                 400

Pro Pro Gly Trp Ala Glu Trp Asn Asp Arg Tyr Arg Asp Thr Val Arg
                405                 410                 415

Ala Phe Trp Lys Gly Asp Glu Gly Met Ala Pro Glu Leu Ala Gly Arg
            420                 425                 430

Ile Thr Gly Ser Gly Gly Asp Phe Asn His Gly Gly Arg Arg Pro Trp
        435                 440                 445

Ala Ser Val Asn Phe Leu Thr Ala His Asp Gly Tyr Thr Leu Asn Asp
    450                 455                 460

Leu Val Ser Tyr Asn Asp Lys His Asn Glu Ala Asn Gly Glu Asp Asn
465                 470                 475                 480

Arg Asp Gly His Ser Asp Asn Arg Ser Trp Asn Cys Gly Ala Glu Gly
                485                 490                 495

Pro Thr Asp Asp Pro Asp Ile Arg Ala Leu Arg Glu Arg Gln Lys Arg
            500                 505                 510

Asn Met Leu Ala Thr Leu Leu Phe Ser Gln Gly Thr Pro Met Ile Val
        515                 520                 525

Ala Gly Asp Glu Phe Gly Arg Thr Gln Gln Gly Asn Asn Asn Ala Tyr
    530                 535                 540

Cys Gln Asp Asn Glu Ile Ser Trp Val Asp Trp Glu Ile Asn Glu Asp
545                 550                 555                 560
```

-continued

```
Gly Ala Ala Leu Ile Glu Phe Leu Arg Lys Leu Thr Thr Leu Arg His
                565                 570                 575

Thr Leu Pro Val Leu Arg Arg Gly Arg Phe Leu Thr Gly Asp Tyr Asp
            580                 585                 590

Glu Ser Met Asp Val Ala Asp Val Lys Trp Leu Ser Ser Ser Gly Glu
        595                 600                 605

Ala Leu Thr Pro Glu Gln Trp Ala Asp Thr Asn Met Arg Cys Phe Gly
    610                 615                 620

Leu Ile Ile Asp Gly Arg Ala Arg Ala Thr Gly Ile Arg Arg Pro Ala
625                 630                 635                 640

Ser Asp Ala Thr Leu Leu Leu Ile Phe Asn Ala Tyr His Asp Val Val
                645                 650                 655

Asp Phe Thr Leu Pro Glu Ile Pro Gly Asn Asp Arg Trp Thr Cys Leu
            660                 665                 670

Ile Asp Thr Asn Ala Pro Val Arg Ala Glu Leu Pro Gln Phe Ala Ser
        675                 680                 685

Gly Asp Val Tyr Gln Val Thr Gly Arg Ser Leu Leu Leu Phe Ser Leu
    690                 695                 700

Gln Ala Lys Gly Pro Thr Gln Arg Val Phe Asp Lys Ile Glu Glu Ala
705                 710                 715                 720

Ile Thr Asp Glu Glu Thr Pro Glu Pro Ala Arg Glu Ala Ala Ala Ile
                725                 730                 735

Val Lys Lys Ser Val Lys Lys Glu Lys Pro Ser Lys
            740                 745
```